United States Patent
Napora et al.

(10) Patent No.: US 10,438,694 B2
(45) Date of Patent: Oct. 8, 2019

(54) MANAGEMENT OF MEDICAL WORKFLOW

(75) Inventors: Brian Napora, Spokane, WA (US); Jon Copeland, Spokane, WA (US); Stephen Duvoisin, Spokane, WA (US); William Keyes, Spokane, WA (US); Dan Murray, Spokane, WA (US); William Schulte, Spokane, WA (US); Gordon Teel, Spokane, WA (US)

(73) Assignee: Medicalis Corporation, Kitchener (CA)

( * ) Notice: Subject to any disclaimer, the term of this patent is extended or adjusted under 35 U.S.C. 154(b) by 1233 days.

(21) Appl. No.: 11/942,652

(22) Filed: Nov. 19, 2007

(65) Prior Publication Data

US 2009/0132586 A1 May 21, 2009

(51) Int. Cl.
| G06F 17/30 | (2006.01) |
|---|---|
| G16H 40/20 | (2018.01) |
| G16H 40/63 | (2018.01) |
| G16H 10/60 | (2018.01) |
| G16H 80/00 | (2018.01) |

(52) U.S. Cl.
CPC ............. *G16H 40/20* (2018.01); *G16H 10/60* (2018.01); *G16H 40/63* (2018.01); *G16H 80/00* (2018.01)

(58) Field of Classification Search
CPC ......... G06Q 50/22; G06Q 50/24; G06F 17/30
USPC ....................................................... 705/3, 2
See application file for complete search history.

(56) References Cited

U.S. PATENT DOCUMENTS

| 5,748,907 | A | * | 5/1998 | Crane ................................. 705/2 |
|---|---|---|---|---|
| 5,974,389 | A | * | 10/1999 | Clark et al. ........................ 705/3 |
| 7,729,928 | B2 | | 6/2010 | Backhaus et al. |
| 8,050,944 | B2 | * | 11/2011 | Brummel .............. G06F 19/322 |
| | | | | 705/2 |
| 2005/0108052 | A1 | * | 5/2005 | Omaboe ............... G06F 19/322 |
| | | | | 705/2 |
| 2005/0114178 | A1 | * | 5/2005 | Krishnamurthy et al. ....... 705/2 |
| 2005/0114283 | A1 | * | 5/2005 | Pearson ................ G06F 19/322 |
| | | | | 706/50 |
| 2006/0074711 | A1 | * | 4/2006 | Mahesh et al. .................... 705/2 |
| 2006/0173858 | A1 | * | 8/2006 | Cantlin ................ G06F 19/321 |
| 2006/0282302 | A1 | * | 12/2006 | Hussain ............................ 705/9 |
| 2007/0050701 | A1 | * | 3/2007 | El Emam et al. ............ 715/505 |
| 2009/0287505 | A1 | | 11/2009 | Wood |

OTHER PUBLICATIONS

Google patents search, Aug. 28, 2015.*
Google patents search, Dec. 30, 2016.*
Google patents search, Aug. 28, 2017.*

* cited by examiner

*Primary Examiner* — Dilek B Cobanoglu
(74) *Attorney, Agent, or Firm* — SBMC

(57) ABSTRACT

Various embodiments provide participants in a medical workflow with an integrated way to interact with a variety of medical information systems. Medical information can be collected from different medical information systems and/or data sources and presented to a user in one or more customized interfaces. Users can interact with the interface(s) and perform tasks associated with a medical workflow.

20 Claims, 29 Drawing Sheets

Slot: Hosp A Radiology                                  July 29, 2007  11:43am

| | | Today TAT | YTD TAT | Variance | Procedures in Q | STAT in Q |
|---|---|---|---|---|---|---|
| Today | | 2204 | 2206 | 2208 | 2210 | |
| Emergency Department | Preliminary Reports | 8.1 | 14.5 | 6.4 | 26 | 5 |
| | Final Reports | 5.5 | 6.2 | 0.7 | 7 | 4 |
| Department (excluding ED) | | 10.0 | 12.6 | 2.6 | | |
| | Preliminary Reports | 8.5 | 9.5 | 1.0 | 19 | 1 |
| | Final Reports | 17.3 | 17.1 | -0.2 | | |
| PROCEDURES COMPLETED TODAY | | 55 | | | | |
| YTD AVERAGE | | 49 | | | | |
| Today's Variance | | 6 | | | | |
| YTD Cumulative Variance | | 222 | | | | |

MANAGEMENT OF MEDICAL WORKFLOW

BACKGROUND

In day-to-day operations, healthcare enterprises receive and transmit tremendous amounts of medical data. Healthcare entities such as doctors' offices, hospitals and medical imaging facilities typically share medical data to ensure proper care and treatment for their patients. However, the effective exchange of medical data presents a two-fold challenge: First, each interested party wishes to have timely access to particular sets of medical data that it requires. Second, the medical data should be presented to each interested party in a user-friendly format that allows the party to quickly recognize and interact with particular data elements of interest.

While many systems for medical data exchange are currently in use, these systems are not standardized and each system presents the user with a different interface and a different user experience. As a consequence, a medical worker who travels between multiple healthcare facilities may be forced to learn several different systems for medical data entry, diagnosis and exchange. Each system typically has its own unique interface and its own unique protocols for entering, sending and receiving medical data, thus forcing the medical worker to learn these different systems and adapt his or her methods accordingly. This decreases the overall efficiency of the medical worker and increases the likelihood that mistakes will be made during a medical data exchange process.

Take, for example, a scenario involving a typical radiological exam utilizing magnetic resonance imaging (MRI). In this scenario, a patient complaining of knee pain visits his or her general practitioner (GP). During this visit, a worker at the GP's office enters the patient's medical information into an electronic medical record (EMR) via the particular medical information system utilized by the GP. The GP, suspecting some type of internal knee injury, schedules an MRI for the patient at an off-site imaging facility. The GP's office must then transfer the patient's medical information and the MRI request to the imaging facility. The imaging facility receives the patient's medical information and the MRI request via its own medical information system and enters the MRI request. The imaging facility then performs the MRI and attaches the resulting MRI image to the patient's medical record as an image in a picture archive.

The MRI image must then be read by a radiologist to determine the extent of the knee injury, if any. A reading room assistant who assists the radiologist receives the MRI image and prepares it for the radiologist to read. The radiologist interprets the MRI image and creates an interpretive and/or diagnostic report based on his or her findings. The findings can then be incorporated into the patient's medical record. As with the GP and the imaging facility, the radiologist may have his or her own specific medical information system that differs from those utilized by the GP and/or the imaging facility.

Based on the radiologist's interpretation of the MRI image, the GP may refer the patient to an orthopedic surgeon to repair the knee injury. The patient's medical record is then forwarded to the orthopedic surgeon, who receives the medical record into his or her own medical information system. The orthopedic surgeon must then interpret the patient's medical information from the record and retrieve the MRI image to determine the proper treatment for the knee injury.

As is evident from this example scenario, the exchange of medical information between parties with disparate medical information systems has the potential to create confusion when one party must interpret another party's protocol for identification and categorization of medical data. Further, by requiring different healthcare entities to interpret and rearrange medical data to suit their own particular systems, the utilization of disparate medical information systems introduces a great deal of inefficiency into processes that require the exchange of medical information.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Various embodiments provide participants in a medical workflow with an integrated way to interact with a variety of medical information systems. Medical information can be collected from different medical information systems and/or data sources and presented to a user in one or more customized interfaces. Users can interact with the interface(s) and perform tasks associated with a medical workflow.

BRIEF DESCRIPTION OF THE DRAWINGS

The same numbers are used throughout the drawings to reference like features.

FIG. 10 illustrates one example of a medical technologist Online Form and one example of a medical image interface in accordance with one or more embodiments.

FIG. 12 illustrates one example of a dispatcher Online Form in accordance with one or more embodiments.

FIG. 22 illustrates one example of a medical facility dashboard for analyzing medical facility workflow in accordance with one or more embodiments.

DETAILED DESCRIPTION

Various embodiments provide techniques and processes for managing medical workflow. In general terms, a medical workflow refers to one or more tasks to be performed to achieve a particular medical objective. The techniques and processes comprise a comprehensive workflow tool that provides medical workers with an integrated and extensible way to interact with medical workflows. According to one embodiment, a participant in a medical workflow selects a medical record to interact with from an external medical information system. In response to the selection of the medical record, a workflow tool launches an Online Form and automatically populates the form with medical data associated with the medical record from the medical information system. The user can edit and/or add to the medical record by interacting with the Online Form. Any changes to the medical record can be pushed out to one or more external systems to update any external instances of the medical record. Tasks associated with the medical record can be monitored by a dispatcher and can be assigned to a medical worker via a dispatcher interface generated and managed by the workflow tool. The described techniques and processes also include scheduling functionality that enables medical resources to be paired with medical workflows and medical tasks.

Operating Environment

Figure 1:
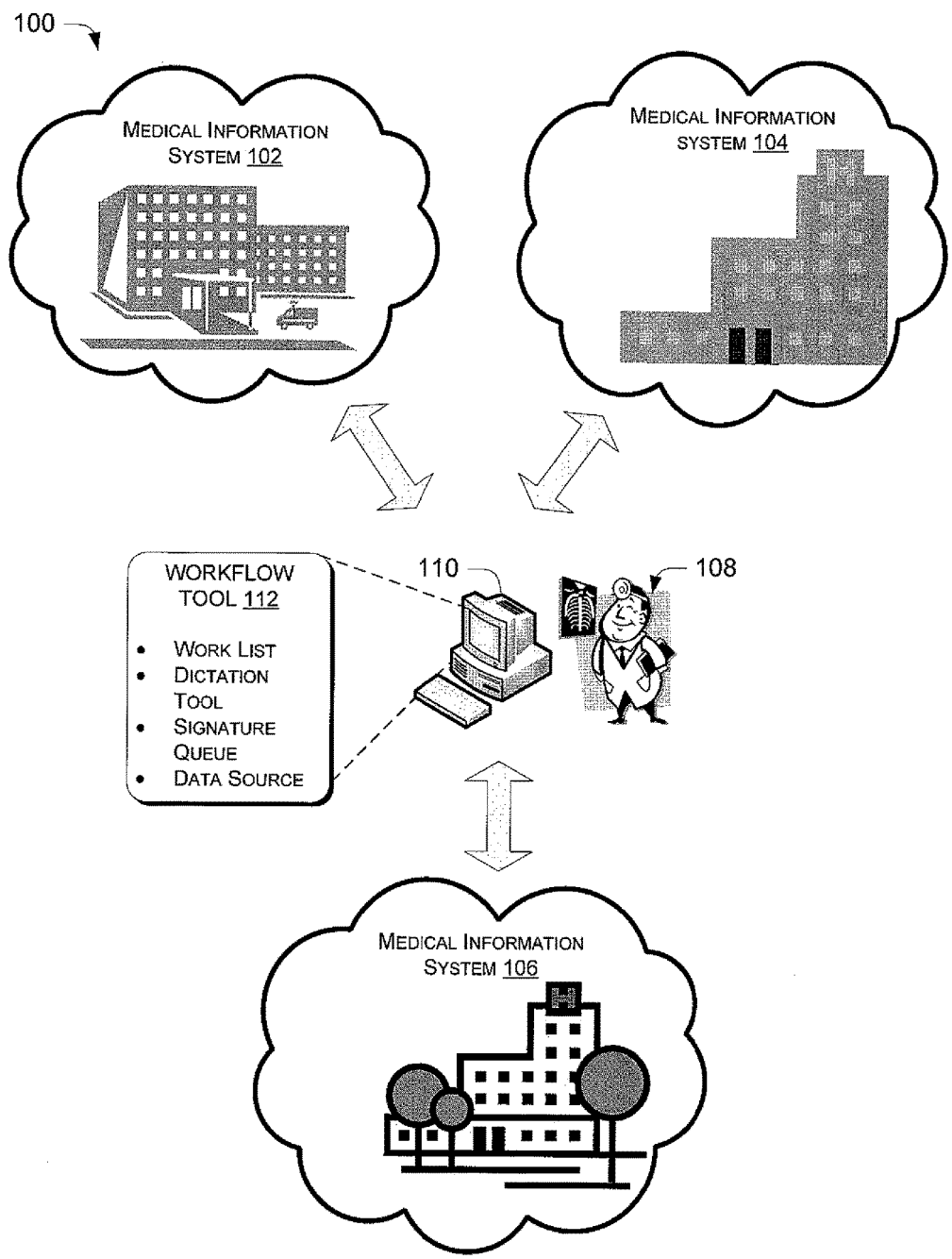
FIG. 1 illustrates an operating environment that can utilize a workflow tool in accordance with one or more embodiments.

FIG. 1 illustrates an operating environment 100 in accordance with one or more embodiments. Operating environment 100 includes several medical information systems (MIS), illustrated as MISs 102, 104, and 106. Each of MISs 102-106 can be associated with a variety of medical facilities, such as hospitals, medical imaging facilities, medical testing facilities, and/or any other facility that can be involved in a medical workflow. These MISs provide the facilities with a means for managing medical data within their own particular facility or network of facilities. As discussed above, each MIS typically has its own unique interface(s) and its own unique protocols for entering and propagating medical data.

Operating environment 100 also includes a medical worker 108, illustrated here as a radiologist. However, medical worker 108 can include any entity that is involved in a typical medical workflow, such as a medical technician, a medical laboratory worker, an imaging technician, a nurse, a general practice physician, a medical specialist, and the like.

In this example, medical worker 108 utilizes a client device 110 to interact with a particular medical workflow. Client device 110 is illustrated here as a desktop computer. However, any suitable device may be utilized, such as a laptop computer, a tablet computer, a personal digital assistant, and the like. Client device 110 can include one or more processors, one or more computer-readable media, and one or more applications that reside on the computer-readable media and which are executable by the processor(s). When executed by the processor(s), the application(s) can implement the processes and techniques described herein. The computer-readable media can include, by way of example and not limitation, all forms of volatile and non-volatile memory and/or storage media that are typically associated with a computing device. Such media can include ROM, RAM, flash memory, hard disk, removable media and the like.

Running on client device 110 is a workflow tool 112, which can implement the processes and techniques described herein. Workflow tool 112 provides medical worker 108 with an integrated application for interacting with a medical workflow. Workflow tool 112 is configured to wrap the various interfaces associated with medical systems 102-106. By wrapping these interfaces, workflow tool 112 can extract information from the systems, as well as push data from the workflow tool to the systems. In interacting with different medical workflows and medical information systems, workflow tool 112 can wrap both data interfaces (e.g., a software interface) and graphical user interfaces. In this example, even though medical worker 108 interacts with MISs 102, 104 and 106, workflow tool 112 presents the medical worker with a single work list, a single dictation tool, a single signature queue, and a single data source. Thus, workflow tool 112 provides a way of aggregating medical workflow data from disparate MISs into a seamless medical workflow process.

Figure 2:
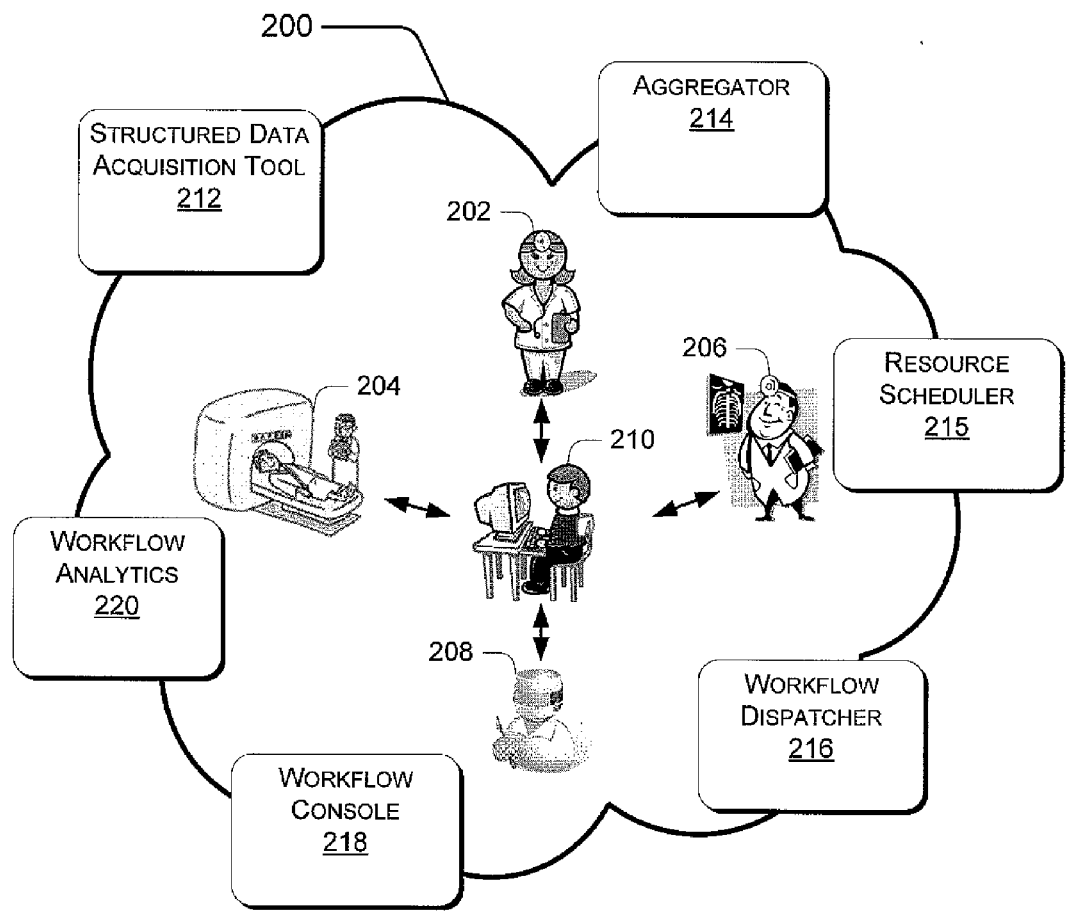
FIG. 2 illustrates an operating environment that can implement certain aspects of a workflow tool in accordance with one or more embodiments.

FIG. 2 illustrates at 200 a collection or "cloud" of medical data that includes a variety of medical workflows in accordance with one or more embodiments. FIG. 2 also illustrates several medical workers who can be involved in a particular medical workflow. The illustrated medical workers include a general practitioner 202, an imaging technician 204, a radiologist 206, and a specialist 208. Also shown is a dispatcher 210 who can monitor medical workflows and interact with the workflows to ensure that medical procedures included in a workflow are performed in a timely manner and by the appropriate personnel.

FIG. 2 illustrates several modules that perform tasks for workflow tool 112 in accordance with one or more embodiments. These modules are introduced here and are discussed in greater detail in the following section.

A structured data acquisition tool 212 provides a mechanism for capturing medical data as part of a medical workflow. An aggregator 214 provides functionality for receiving and processing data for the workflow tool 112. A resource scheduler 215 enables the scheduling of medical personnel and/or physical resources (e.g., particular medical facilities) within a particular medical workflow. A workflow dispatcher 216 takes data elements acquired during a workflow and routes the data elements to the appropriate entity and/or workflow container. A workflow console 218 provides graphical user interfaces that enable medical workers to interact with workflow tool 112. Finally, a workflow analytics module can perform statistical analysis of workflow data to enable medical enterprises and other entities to optimize their workflow processes.

The workflow tool modules can be implemented in a variety of ways and by a variety of entities. Particular medical workers can utilize one, several, or all of the modules to accomplish a particular task within a medical workflow. The modules need not be implemented at a single location, and can be distributed among several entities and/or locations to achieve the overall management of medical workflows. In one example, the described processes and techniques can be implemented by a central workflow server that can distribute tasks and workflow tool module functionality to remote resources (e.g., a client device) via a network. Entities that participate in a medical workflow (e.g., medical workers and medical facilities) can communicate via a network. Suitable networks include a local access network (LAN), a wide area network (WAN), the Internet, and so on. In some examples, the described user interfaces can be implemented as web pages in a web-based utilization scenario.

The Workflow Tool

Figure 3:
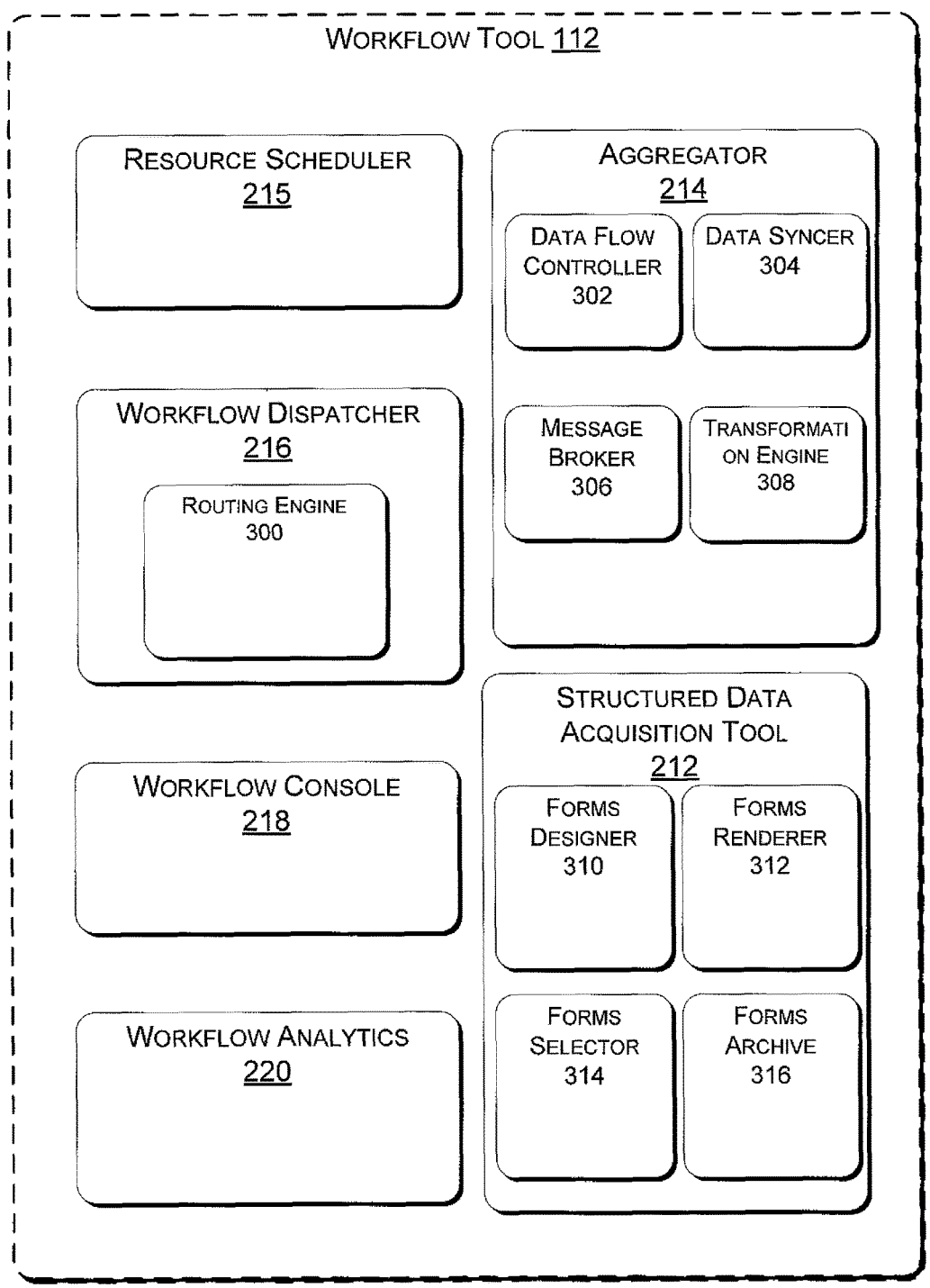
FIG. 3 illustrates a workflow tool in accordance with one or more embodiments.

FIG. 3 illustrates a workflow tool 112 in accordance with one or more embodiments. Workflow tool 112 includes, in this example, several modules that implement the tool's functionality. The workflow dispatcher 216 includes a routing engine 300 that applies rules to data elements received during a medical workflow. In some instances, the rules are applied to determine a particular workflow container that a data element should be routed into. Thus, in one example, a medical procedure represents a data element in a medical workflow. Routing engine 300 can process the data element and determine the type of medical procedure represented by the data element. Routing engine 300 then places the medical procedure data element in an appropriate workflow container such that the medical procedure is routed to the correct entity(s).

Workflow tool 112 also includes workflow console 218. As mentioned above, workflow console 218 provides graphical user interfaces that enable medical workers to interact with workflow tool 112. Workflow console 218 can graphically represent the various containers that make up a particular medical workflow. Each container within a medical workflow represents a particular medical procedure that can be interacted with by entities within the workflow. Workflow console 218 is the gateway into workflow tool 112 and enables medical workers to view and/or manipulate particular medical procedures, manage medical workflow (e.g., by interacting with workflow dispatcher 216), and manually assign procedures into particular workflow containers. Workflow consoles 218 can also provide a consolidated view of the status of various user roles within workflow tool 112, as well as the status of medical procedures being monitored by the workflow tool.

Introduced above, aggregator 214 includes several sub-modules that process data elements received by workflow tool 112 as part of a medical workflow. A data flow controller 302 acts as the master data controller within aggregator 214, and is discussed in more detail below. The Data syncer 304 evaluates each change that occurs to the data and pushes those changes out to each subscribed client. A message broker 306 handles communications between other applications and workflow tool 112. A transformation engine 308 provides for rules-based manipulation of data elements within a medical workflow. Transformation engine 308 enables workflow tool administrators to create custom rules for the handling of data elements.

Workflow tool 112 also includes structured data acquisition tool 212. As mentioned above, the structured data acquisition tool 212 provides a mechanism for capturing data elements as part of a medical workflow. In some implementations, the structured data acquisition tool enables the creation and management of forms known as "Online Forms". In one implementation, Online Forms are electronic forms that provide a data entry mechanism and can receive manual input from users of workflow tool 112. Online Forms can also automatically capture data from external applications that interact with the workflow tool. To achieve this functionality, structured data acquisition tool 212 includes several sub-modules. A forms designer 310 enables users to create custom Online Forms that conform to the needs of particular users or groups of users. A forms renderer 312 renders particular Online Forms that are called as part of a medical workflow. Forms selector 314 contains logic that enables the appropriate form(s) to be called for a particular user. A forms archive 316 serves as a repository for Online Forms.

Workflow tool 112 includes workflow analytics module 220 that can perform business processing on data received and/or generated by workflow tool 112. Workflow analytics module 220 can analyze statistics related to a particular workflow or group of workflows, and can generate reports based on this analysis. These reports can be viewed by entities concerned with workflow statistics.

As part of workflow tool 112, resource scheduler 215 enables medical personnel and physical resources to be scheduled. Resource scheduler 215 can interact with workflow dispatcher 216 to allocate medical tasks and medical workflows to particular medical personnel and medical facilities. A variety of user interfaces can be associated with the resource scheduler, and these interfaces enable the manipulation of medical workflow scheduling. This aspect of workflow tool 112 is discussed in more detail below.

Figure 4:
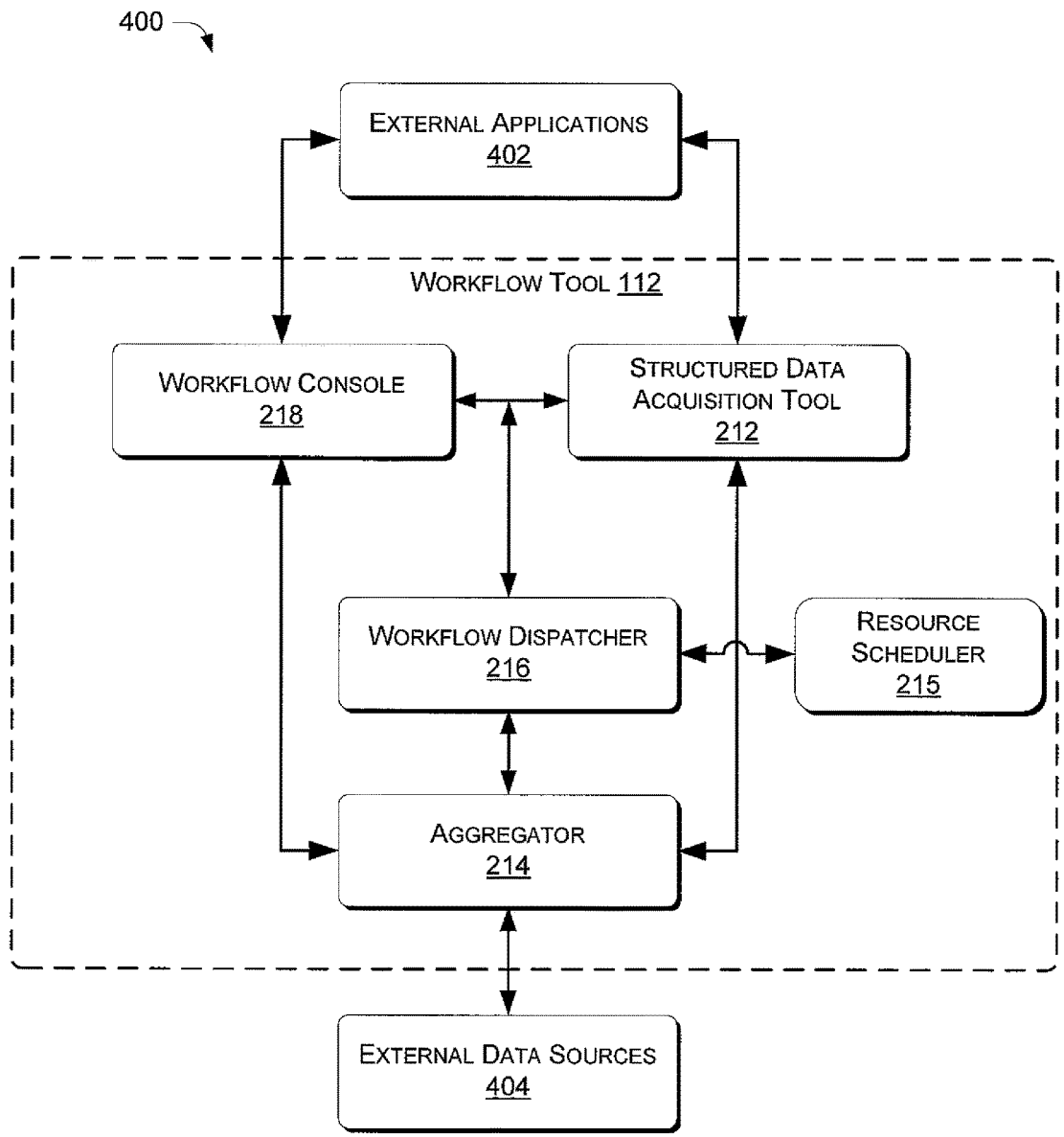
FIG. 4 is a flow diagram that illustrates data flow into, within, and out of a workflow tool in accordance with one or more embodiments.

FIG. 4 illustrates generally at 400 one example of data flow into, within, and out of workflow tool 112, in accordance with one or more embodiments. FIG. 4 includes external applications 402, which are any variety of MISs. Examples of external applications 402 include picture archiving and communications systems (PACS), radiology information systems (RIS), digital imaging and communications in medicine (DICOM) systems, and the like. As shown, data can flow from external applications 402 into the workflow tool via structured data acquisition tool 212 (e.g., through on Online Form), or via workflow console 218. In one example, workflow tool 112 wraps an external application via an Online Form, and the Online Form extracts medical data from the external application for processing by the workflow tool. This aspect of the workflow tool is discussed in more detail below.

Medical data captured by workflow console 218 and/or structured data acquisition tool 212 can be forwarded to aggregator 214. Aggregator 214 can perform normalization and rules-based transformations of the medical data, and can also forward medical data to workflow dispatcher 216. Workflow dispatcher 216 applies rules-based processing to medical data to determine which workflow(s), if any, the data should be directed into.

Also illustrated in FIG. 4 are external data sources 404, which represent any input of medical data that does not directly come through workflow console 218 or structured data acquisition tool 212. Examples of external data sources 404 include data messages and data pulls from external sources (e.g., from an SQL or other suitable database). A data message is a data element or data stream transmitted and/or originating from an external source. With reference to medical data, a data message can include an update, deletion, and/or creation of a medical record. In one example, data pulls refer to receiving data in response to a request for data. Aggregator 214 can be configured to receive data directly from external data sources 404.

Figure 5:
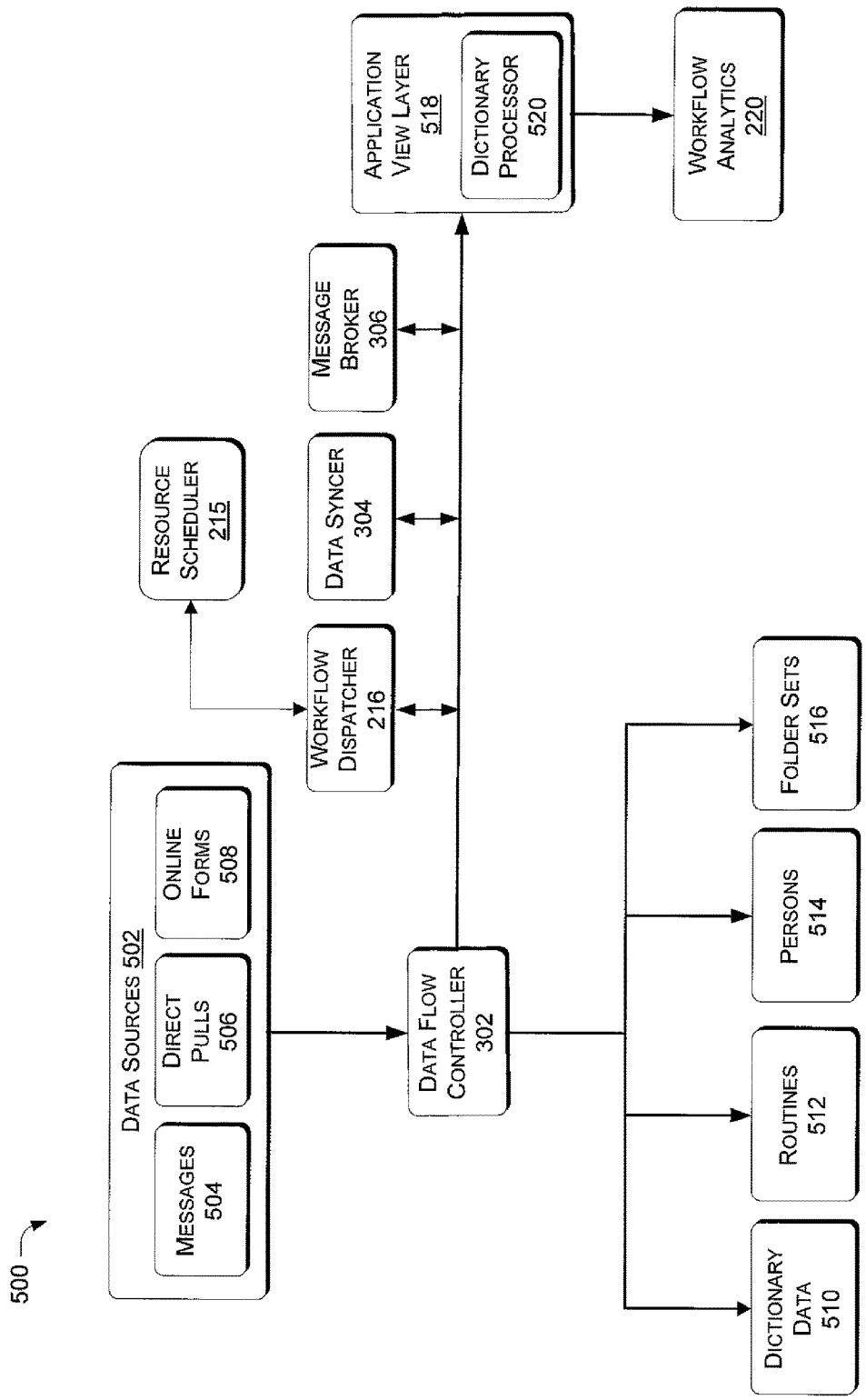
FIG. 5 is a flow diagram of data flow that implements certain aspects of a workflow tool in accordance with one or more embodiments.

FIG. 5 illustrates at 500 one example of data flow within workflow tool 112 in accordance with one or more embodiments. Data sources 502 represent any suitable source of medical data, including data messages 504, direct pulls 506, and Online Forms 508. Data from data sources 502 is received by data flow controller 302. Data flow controller 302 is configured to perform normalization of medical data, as well as make data routing decisions within workflow tool 112. As part of its normalization functionality, data flow controller 302 parses data from data sources 502 and, if appropriate, routes the data to a suitable destination. The destination can include dictionary data 510, routines 512, persons 514, and folder sets 516. Dictionary data 510 includes any lookup or type value that is a part of the procedure information. Routines 512 include procedures that can occur during a given medical workflow. Routines 512 can include actual medical procedures (e.g., medical exams, medical imaging, and the like), and can also include data flow and processing procedures. Persons 514 can include entities (both real and virtual) that are designated to receive medical data. Folder sets 516 represent one way of storing medical data that enables the data to be easily catalogued and accessed. Folder sets 516 are discussed in more detail below.

Data flow controller 302 also routes medical data to a variety of modules that can perform processing of the medical data. Among these modules are resource scheduler 215, workflow dispatcher 216, data syncer 304 (discussed above), as well as message broker 306. Message broker 306 analyzes medical data to determine if the data should be forwarded to any external entities. In one example, message broker 306 can determine that a particular data element should be sent to a speech capture application. Thus, message broker 306 can automatically forward medical data received during a medical workflow to external applications and thereby obviate the need to repeat certain data entry during a particular workflow.

An application view layer 518 serves as a denormalizer for normalized medical data and includes a dictionary processor 520. Dictionary processor 520 helps reconcile medical data that originates from a variety of MISs. Each MIS typically uses its own set of dictionary codes to refer to particular aspects of a medical workflow, and thus similar medical procedures may be referred to by different codes across a variety of systems. For example, MIS 102 may refer to a magnetic resonance imaging procedure using the code "MRI", whereas MIS 104 may refer to the procedure with the code "MR". Dictionary processor 520 is configured to recognize that the two different codes refer to the same general procedure and to ensure that a data element marked with either code is routed to any entity and/or location designated to receive data elements relating to magnetic resonance imaging procedures. This example is for purposes of illustration only, and dictionary processor can handle any type of dictionary code, such as anatomical codes, location codes, personnel codes, and the like.

Denormalized medical data can be forwarded to workflow analytics module 220, which can perform statistical analysis of medical data and generate reports based on the statistical analysis. Examples of statistical analysis and reports are discussed below in the "Workflow Analytics" section.

Folder Sets

Figure 6:
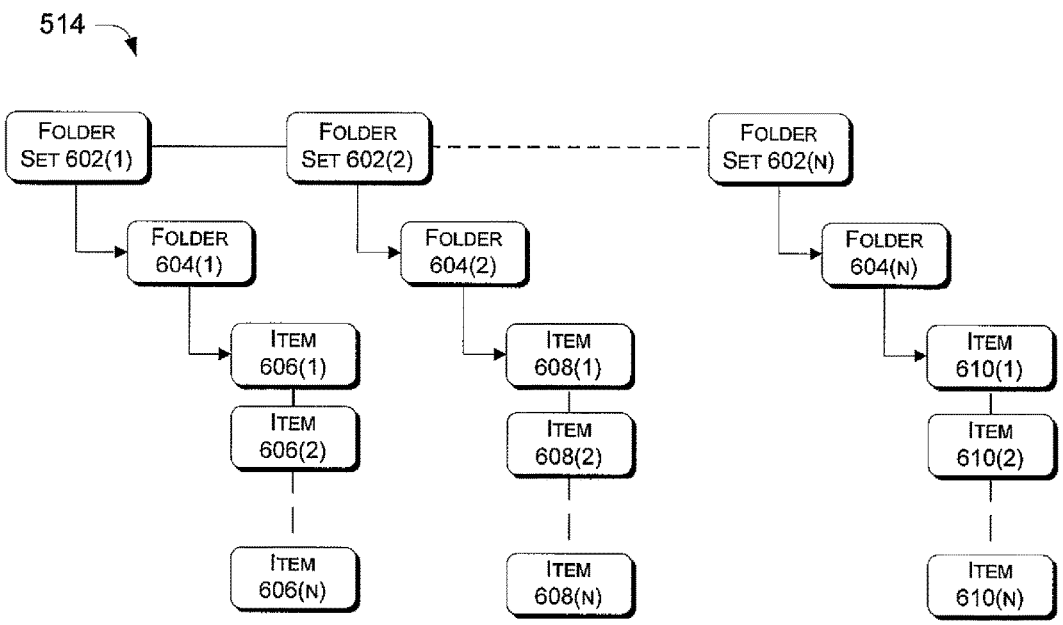
FIG. 6 illustrates one example of folder sets for data handling and storage in accordance with one or more embodiments.

FIG. 6 illustrates one implementation of folder sets 516 in accordance with one or more embodiments. Folder sets 516 represent a more cost-effective technique of handling medical data than those provided by traditional database methods. Folder sets 516 allow particular data elements to be quickly located and updated without the need to traverse large amounts of unrelated data. In this example, each of folder sets 602(1), 602(2), and 602(N) represents a category of medical data. Each folder set can refer to specific procedures, persons, anatomical regions, workflows, and so on. Each of folders 604(1), 604(2), and 604(N) are data flows or particular attributes within their respective folder set. Each of items 606(1)-606(N), 608(1)-608(N), and 610(1)-610(N) is a member or entity that has the particular attribute and/or is part of the particular workflow indicated by the folder with which it is associated.

In one example, folder set 602(1) represents a set of MRI exams and folder 604(1) corresponds to cranial MRI exams. Each of items 606(1), 606(2), and 606(N) contain identifiers for individual patients who have received cranial MRI exams. Thus, if a user of workflow tool 112 wishes to add a patient to a particular medical workflow that includes a cranial MRI, the user simply traverses the folder sets to locate folder set 602(1), traverses the folders within folder set 602(1) to locate folder 604(1), and adds an item corresponding to an identifier for the patient to folder 604(1). Folder sets can be used for attributes of medical workflows that are typically updated on a frequent basis.

Figure 7:
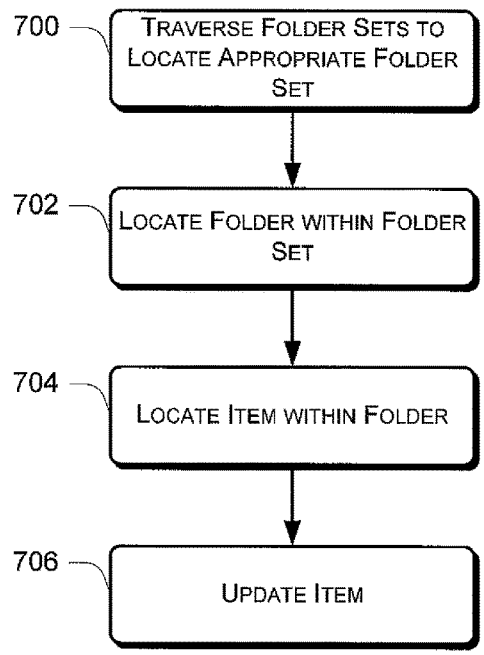
FIG. 7 is a flow diagram of one process for handling data with folder sets in accordance with one or more embodiments.

FIG. 7 illustrates one example of a process for updating items in a medical workflow using folder sets. The method can be implemented in connection with any suitable hardware, software, firmware or combination thereof. In at least some embodiments, the method can be implemented by data flow controller 302. At 700, a plurality of folder sets is traversed to locate an appropriate folder set. At 702, the folders within the appropriate folder set are traversed to locate the appropriate folder. At 704, the items within the appropriate folder are traversed to locate the appropriate item. At 706, the located item is updated. Updating an item can include the addition, deletion, or modification of an item.

WORKFLOW EXAMPLES

This section presents one example of a typical medical workflow from the perspective of the user interfaces encountered by different medical workers in accordance with one or more embodiments. These interfaces are presented for purposes of discussion only, and other workflows and interfaces can be utilized without departing from the spirit and scope of the claimed embodiments. In some embodiments, these interfaces can be generated and/or exposed by workflow console 218, discussed above.

Figure 8:
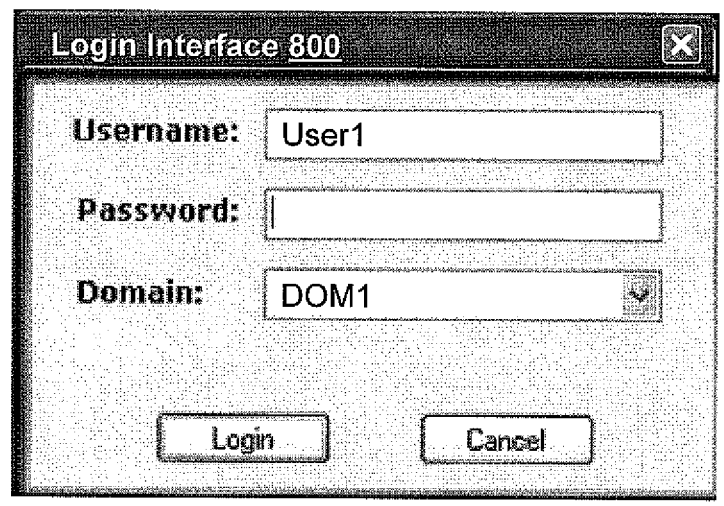
FIG. 8 illustrates one example of a medical information system login interface in accordance with one or more embodiments.

FIG. 8 illustrates one example of a MIS login interface 800 that enables a medical worker to interact with a medical workflow in accordance with one or more embodiments. Interface 800 includes a username field for entering the user name associated with a particular medical worker. The interface also includes a password field for entering the medical worker's password. The domain field allows a medical worker to select a particular domain in which the worker wishes to operate. If the medical worker's username, password, and domain selection correspond to a user profile recognized by the MIS, the medical worker will be logged onto the MIS. While not expressly illustrated here, workflow tool 112 can wrap login interface 800 such that a successful login to the MIS also logs the user into workflow tool 112.

Figure 9:
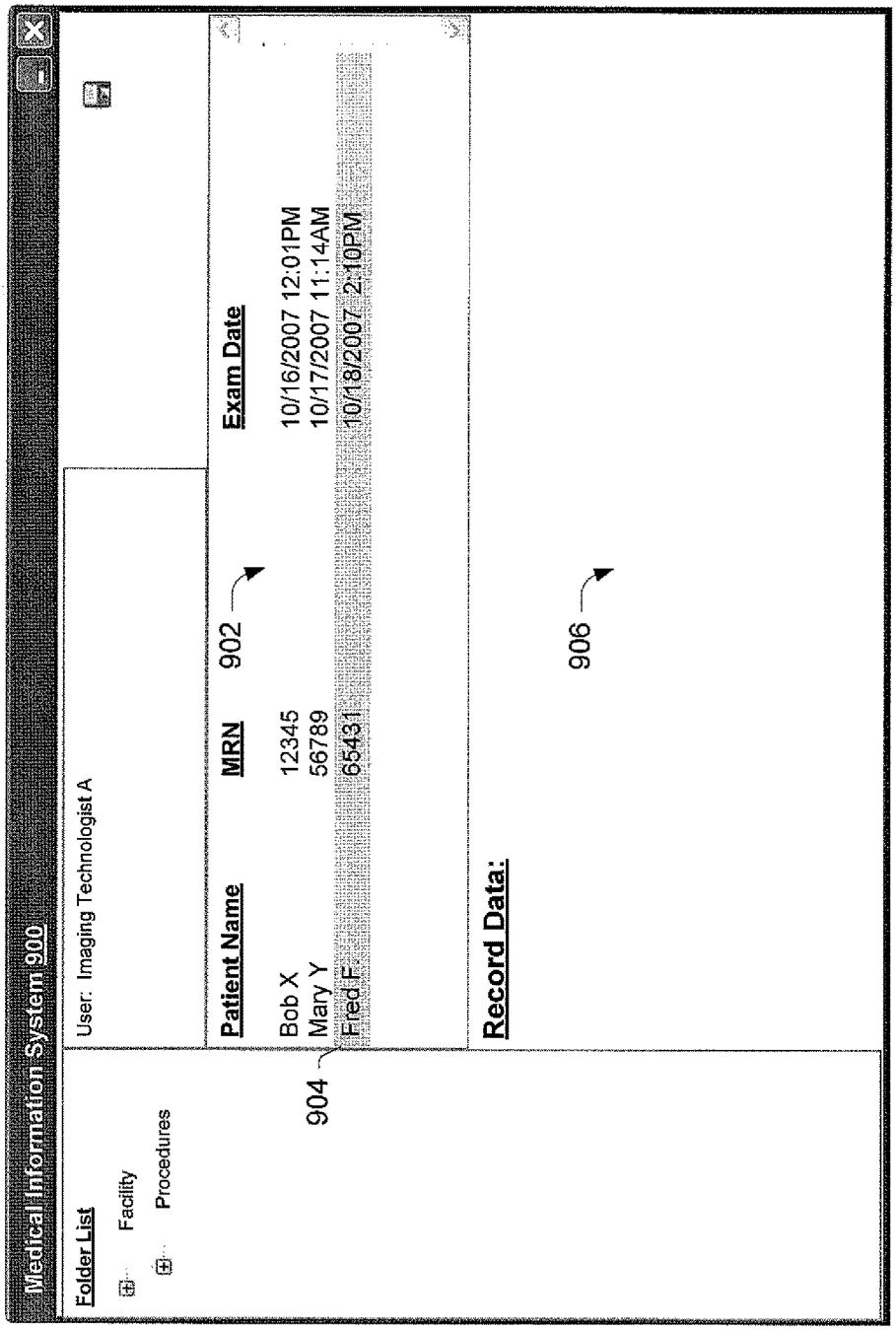
FIG. 9 illustrates one example of a medical information system user interface in accordance with one or more embodiments.

FIG. 9 illustrates one example of an MIS interface 900 in accordance with one or more embodiments. When a medical worker successfully logs onto an MIS (e.g., via login interface 800), the medical worker is presented with MIS interface 900. MIS interface 900 enables the medical worker to interact with medical records contained within and/or accessible to the MIS. These medical records can represent all of part of a particular medical workflow.

Part of MIS interface 900 includes a records field 902 that displays information pertaining to medical records. In this example, records field 902 includes, for each medical record, a patient name, a medical record number (MRN), and a date for an examination of the patient. This interface is presented for illustration purposes only, and other MIS interfaces may contain different types and arrangements of data fields. Shown in records field 902 is a medical record 904 for a patient named "Fred F.". Medical record 904 has been chosen by the particular user of MIS interface 900, as indicated by the darkened background behind the record information. MIS interface 900 also includes a record data field 906. This field can be populated with a variety of information about a particular selected medical record, including medical examination information, medical images, patient history and other medical workflow data.

In this example, the medical worker desires to interact with a medical workflow represented by medical record 904. To do so, the medical worker selects the record (e.g., via a mouse click on medical record 904).

Figure 10:
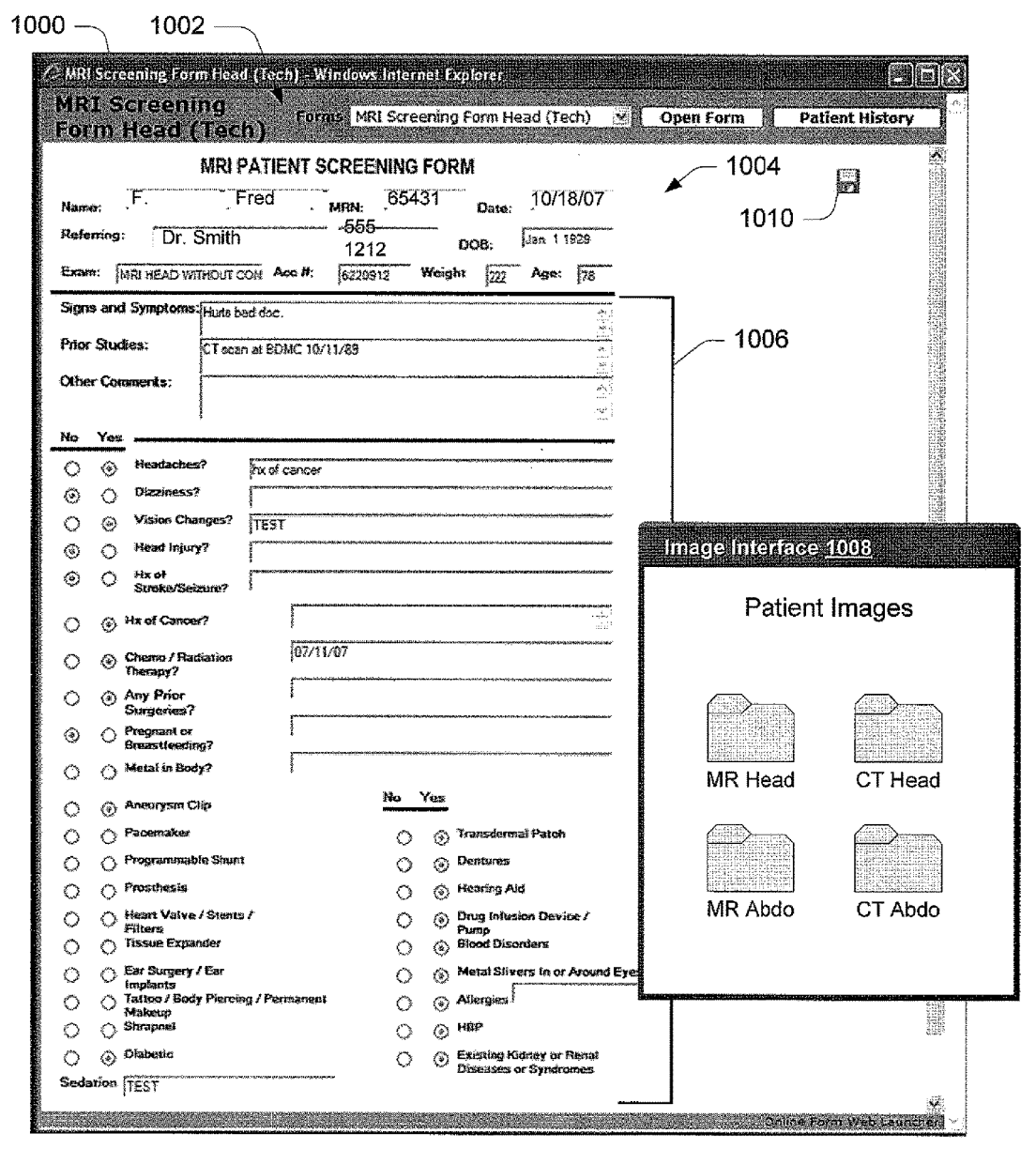

FIG. 10 illustrates one example of an Online Form 1000 that can be launched and displayed to the medical worker in response to the worker's selection of a medical record (e.g., the worker's selection of medical record 904, discussed above), in accordance with one or more embodiments. By wrapping MIS interface 900, workflow tool 112 detects a user's selection of a particular medical record and can launch an appropriate Online Form in response to the selection of the medical record. Workflow tool 112 can determine the appropriate Online Form to launch based on any number or criteria, including a medical worker's login information, the medical worker's role in a particular medical workflow, the task to be completed by the medical worker, and so on. When Online Form 1000 is launched, workflow tool 112 can automatically capture medical data from MIS interface 900 (or any other data source) and populate Online Form 1000 with the data.

As indicated in a header 1002 of Online Form 1000, this example of an Online Form corresponds to a technologist ("tech") role in the particular medical workflow associated with Online Form 1000. Thus, the Online Form will display data fields and task options relevant to the technologist role, and can exclude those fields not required by a technologist and/or those that the technologist is not permitted to view or interact with based on the technologist's user permissions.

Online Form 1000 includes personal data region 1004, which contains several fields for entry of patient personal information (e.g., patient name, the name of any referring doctor, the patient's date of birth, and so on). A medical data region 1006 lists specific medical information, such as signs and symptoms displayed by the patient, any prior studies conducted, and so on. Medical data region 1006 includes a variety of data fields where observations and comments can be entered by medical workers who interact with the form. Medical data region 1006 also includes a variety of radio buttons that can be selected to choose specific medical symptoms or other physical conditions.

When Online Form 1000 launches in response to a user selection of a medical record, an image interface 1008 can automatically be launched. Image interface 1008 contains images generated by diagnostic procedures performed in relation to the medical record. In this example, image interface 1008 includes files that contain several different types of medical images, including MRI images of the patient's head ("MR Head"), computed tomography ("CT") images of the patient's head ("CT Head"), MRI images of the patient's abdomen ("MR Abdo"), and CT images of the patient's abdomen ("CT Abdo"). Image interface 1008 can be launched by an external application, or by workflow tool 112.

In this example, the medical worker can enter and/or edit information via Online Form 1000. As shown here, the worker enters into the "Signs and Symptoms" field the text "Hurts bad doc". Other fields, such as the "Prior Studies" field, can be automatically populated with information from MIS interface 900. If the medical worker performs any imaging procedures, the worker can save the resulting images in image interface 1008. This will link the images to medical record 904 and the medical workflow associated with Online Form 1000. For purposes of this example, the medical worker (e.g., an MRI technician) has performed a medical imaging procedure on patient "Fred F." and has submitted the resulting images along with Online Form 1000.

When the medical worker is finished interacting with Online Form 1000, the worker can click a save button 1010. This saves the data from Online Form 1000 to a suitable data storage location and submits the data to other functionalities within workflow tool 112 for processing, such as aggregator 214 and workflow dispatcher 216. Workflow dispatcher 216 can analyze the data and determine an appropriate destination for the data. Workflow tool 112 can detect the images attached to the data and forward the data and images to an appropriate entity to be analyzed.

Figure 11:
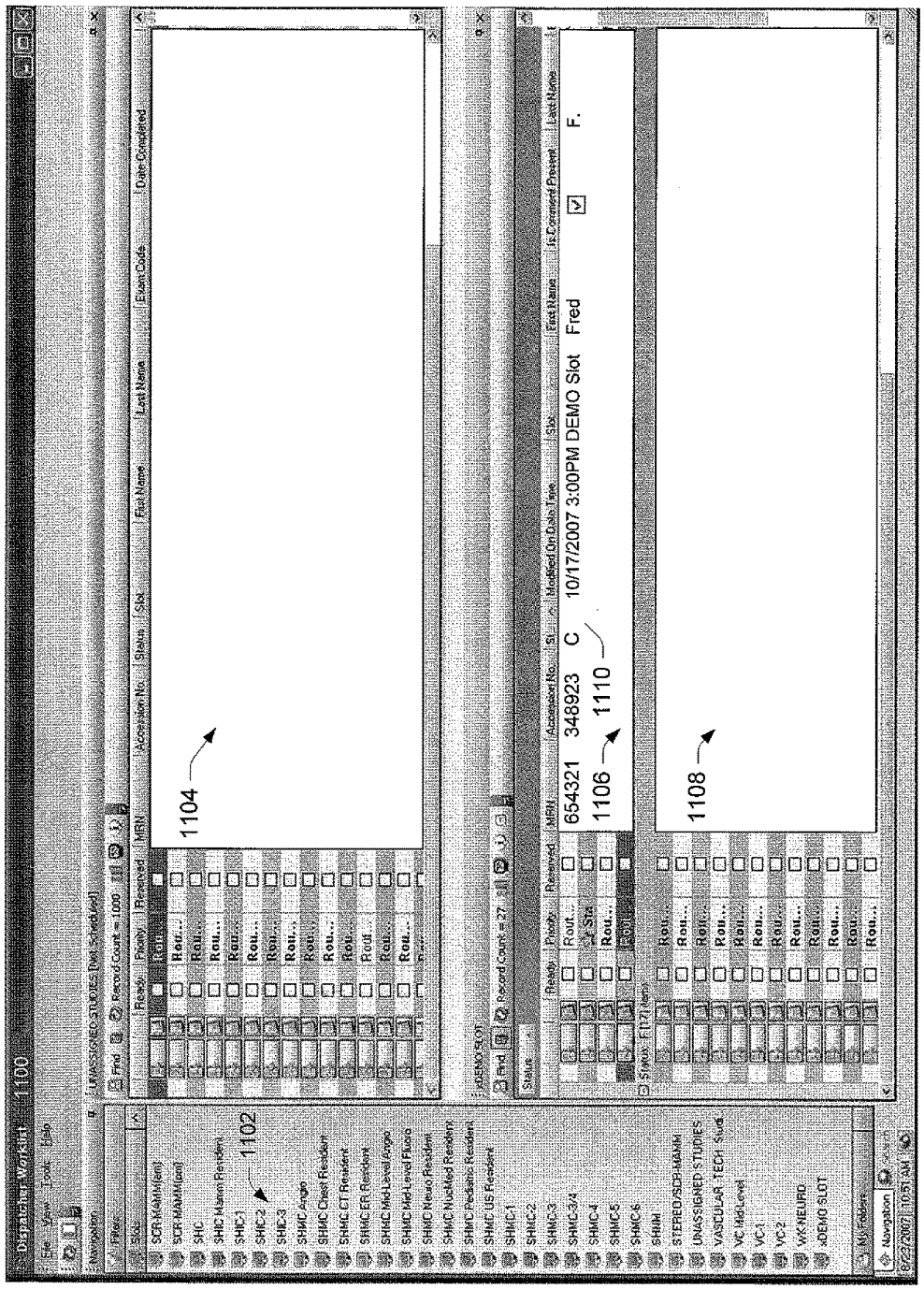
FIG. 11 illustrates one example of a dispatcher worklist interface in accordance with one or more embodiments.

FIG. 11 illustrates a dispatcher interface 1100 that can be used to manage a variety of medical workflows, in accordance with one or more embodiments. Dispatcher interface 1100 can receive medical records and task requests from a variety of data sources and interfaces, and can act as a monitoring facility for multiple tasks associated with different medical workflows. In one implementation, dispatcher interface 1100 is generated by workflow console 218. A human user can interact with dispatcher interface 1100 to ensure that medical tasks and workflows are performed accurately and in a timely fashion.

Dispatcher interface 1100 includes several regions for the display of information. A slot menu 1102 displays slots that can contain a variety of medical task records and/or medical workflows. Slots can be used to assign medical tasks to specific facilities and/or personnel. Slots can include a specific medical facility, a specific medical worker, a medical procedure, a medical specialty, and so on. A medical task can be assigned to a specific slot, indicating that the task is to be completed by the entity associated with the slot. In some implementations, slots can be manipulated (e.g., added, deleted, or otherwise edited) using folder sets.

An unassigned studies region 1104 displays task records that have not yet been assigned to a slot. A user of dispatcher interface 1100 can review a task record in unassigned studies region 1104 and assign the record to an appropriate slot. In one example, this can be done by dragging and dropping the task record from unassigned studies region 1104 into the appropriate slot in slot menu 1102.

Dispatcher interface 1100 also includes a slot record region 1106 that displays task records that have been assigned to a specific slot. In this example, the slot name is shown as "xDemo Slot" (as shown in the header of this region), and the records listed in this region have been assigned to this slot. A finished records region 1108 displays task records that have been finished. For example, if a certain task requires that a set of MRI images be reviewed by a radiologist, once the radiologist has reviewed the images and entered his or her findings, the radiologist can mark the task as complete and the task will be moved into finished records region 1108.

In operation, and with reference to the example discussed above in FIG. 10, workflow dispatcher 216 determines an appropriate routing location for a workflow associated with the medical data from Online Form 1000. Workflow dispatcher 216 submits the data to workflow console 218, which populates dispatcher interface 1100 with a task record 1110 indicating that a workflow exists with an outstanding task to be performed. In one implementation, task record 1110 is automatically assigned to a slot by workflow dispatcher 216. In another implementation, as user of dispatcher interface 1100 can manually assign the task record to an appropriate slot.

In this example, the outstanding task indicated by task record 1110 includes medical images of patient Fred F. that need to be read by a radiologist. A user of dispatcher interface 1100 can click on task record 1110 to open and interact with the record.

Figure 12:
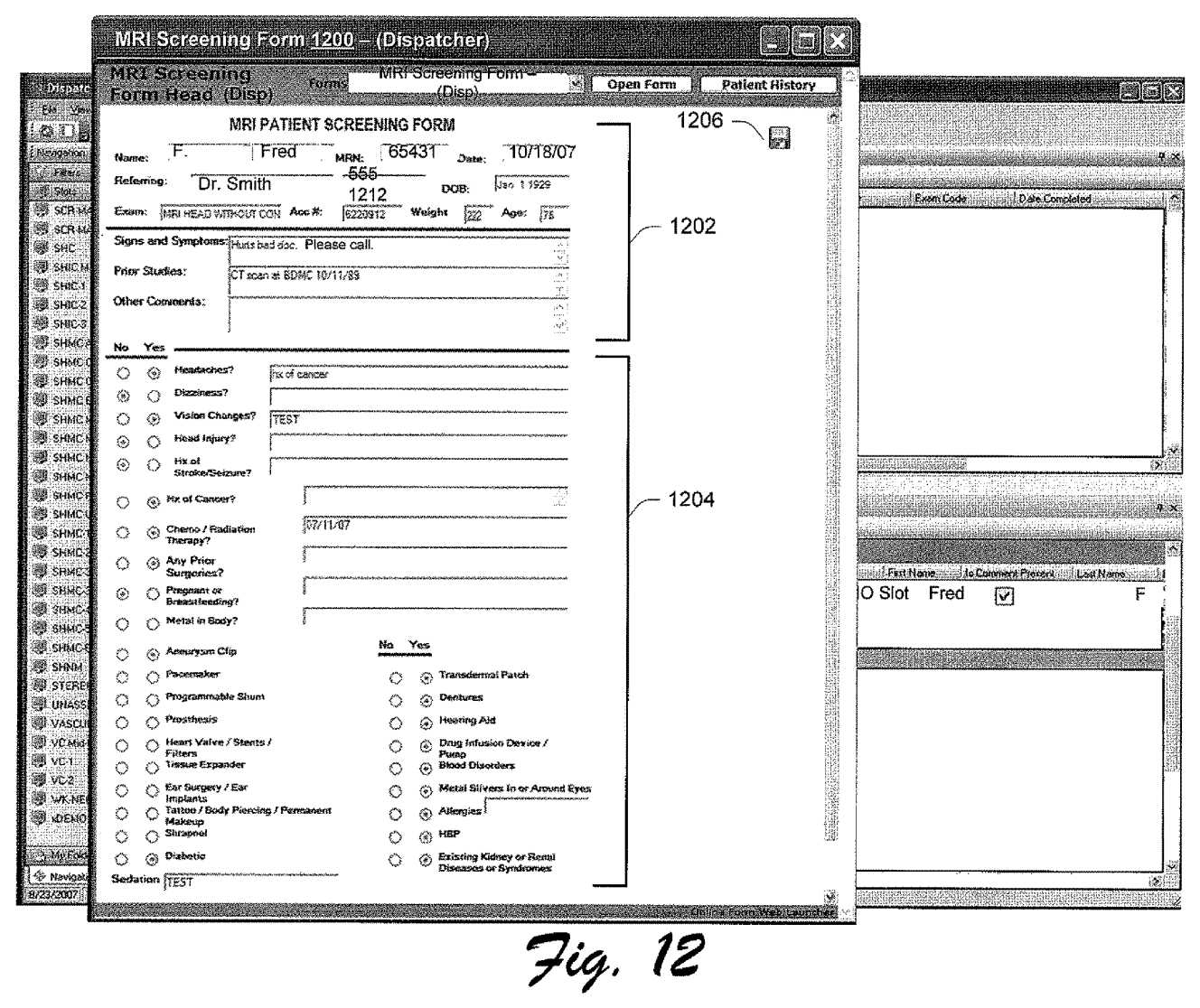

FIG. 12 illustrates a dispatcher Online Form 1200 that can be displayed in response to opening task record 1110 from dispatcher interface 1100, in accordance with one or more embodiments. As indicated in the header of this form, the form has been configured for a dispatcher role in a medical workflow. Dispatcher Online Form 1200 is automatically populated with patient information collected during previous medical procedures and consultations. Workflow tool 112 can harvest data from dispatcher interface 1100 and/or an external MIS to populate dispatcher Online Form 1200.

Dispatcher Online Form 1200 includes a personal data region 1202, where personal data about a patient can be entered and displayed. The form also includes a medical data region 1204, where medical data about a patient can be entered and displayed. In this example, a user of dispatcher Online Form 1200 has entered a comment into the "Signs and Symptoms" field of the form indicating "Please call", which requests that a medical worker involved with this patient's workflow contact the patient. When a user has finished interacting with dispatcher online form 1200, the user can select a save icon 1206. This saves the data from the form to the patient's medical record. Selecting save icon 1206 can also push the data out to an external MIS to update a record associated with the patient.

Referring back to dispatcher interface 1100 in FIG. 11, a user of the dispatcher interface can mark task record 1110 as ready to be read by selecting the "ready" checkbox associated with the record. In one example, designating a task record as "ready" pushes the task record out to another medical worker who can interact with the workflow associated with the task record.

Figure 13:
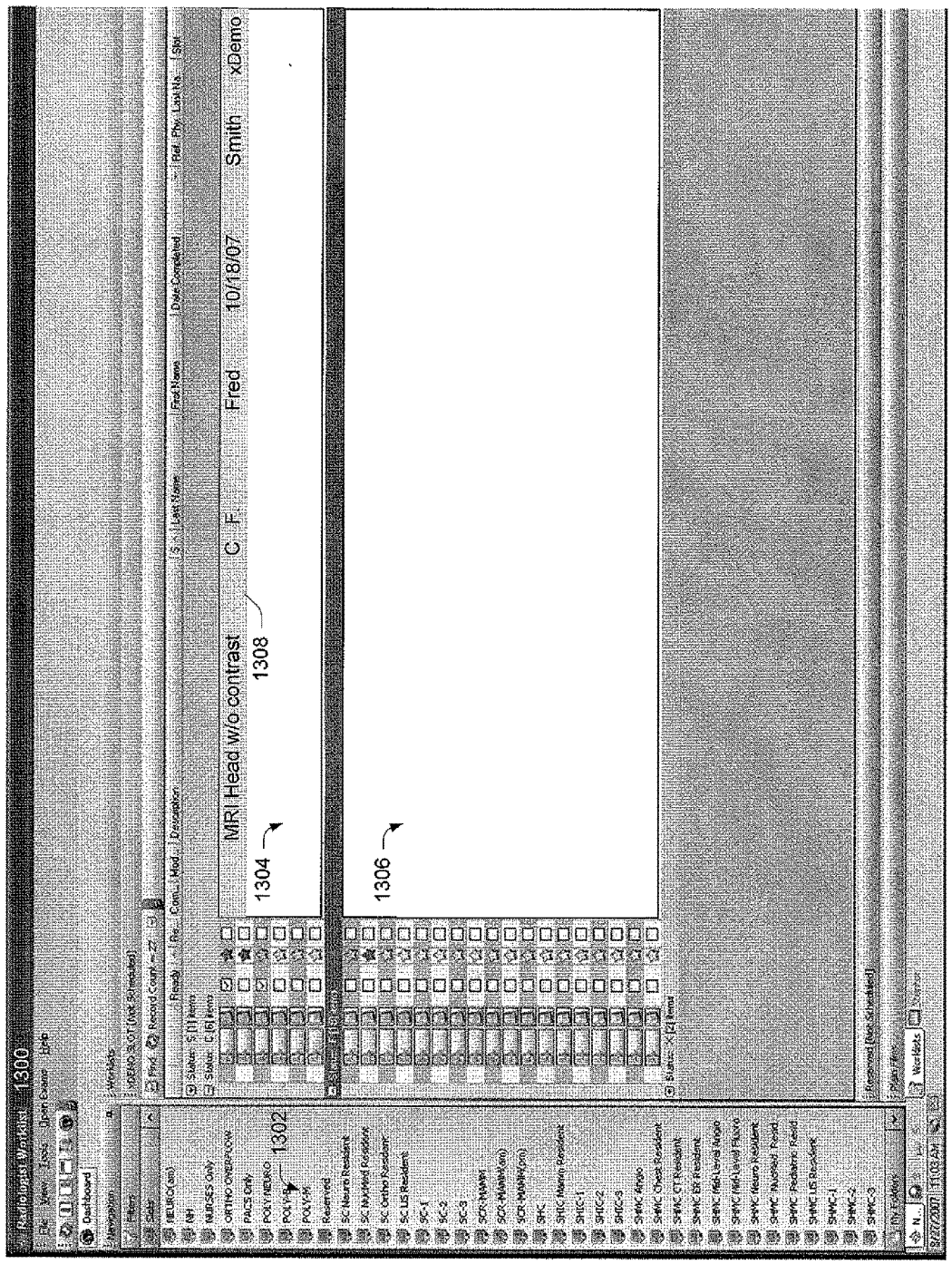
FIG. 13 illustrates one example of a radiologist worklist interface in accordance with one or more embodiments.

FIG. 13 illustrates a radiologist interface 1300 which can display medical records and medical tasks for a radiologist, in accordance with one or more embodiments. A radiologist is used here for purposes of example only, and this interface can be adapted for a variety of medical workers without departing from the scope and spirit of the claimed embodiments. For example, this interface can be adapted for use by cardiologists, oncologists, neurologists, and any other medical professional.

Radiologist interface 1300 includes a slot menu 1302, which is similar in function to slot menu 1102, discussed above. Slot menu 1302 enables a radiologist to navigate between slots (e.g., by selecting individual slots) and view tasks and workflows associated with a slot. The interface also includes a completed task region 1304 and a finished task region 1306. Completed task region 1304 includes medical tasks and/or workflows that have been completed by medical workers other than the radiologist (e.g., an MRI technician) and are waiting to be worked on by the radiologist. Finished task region 1306 includes medical tasks and/or workflows that have been worked on by the radiologist and have been designated as finished. The interface also includes a task record 1308 associated with patient Fred F. Task record 1308 indicates that the record includes an image of an "MRI head without contrast" that is waiting to be read by the radiologist. Task record 1308 also indicates the referring doctor ("Smith") and the slot in which the task exists ("xDemo"). To interact with task record 1308, the radiologist can select the record (e.g., by clicking on the record with a mouse and pointer).

Figure 14:
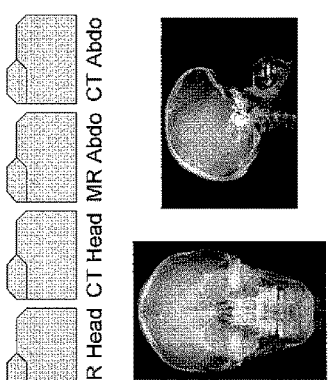
FIG. 14 illustrates one example of a medical image interface, a radiologist online form, and a speech capture interface in accordance with one or more embodiments.

FIG. 14 illustrates several interfaces that can be displayed in response to the radiologist selection of task record 1308, in accordance with one or more embodiments. Included in these interfaces are an image interface 1400, a radiologist Online Form 1402, and a speech capture interface 1404. These three interfaces are displayed as one example only, and other implementations can display one, several, or all of these interfaces.

Image interface 1400 includes image files associated with the selected task record. The image files can include links to images stored at a remote storage facility, files containing the digital images, tiles of the actual images, and so on. In this example, image interface 1400 includes several images of patient Fred F., including an MRI head, a CT head, an MRI abdomen, and a CT abdomen. Image interface 1400 can be generated by workflow tool 12, or can be generated by an external MIS and launched in response to the radiologist's section of a task record from radiologist interface 1300.

Radiologist Online Form 1402 is configured specifically for the role of the radiologist and can launch automatically in response to the radiologist's selection of task record 1308.

This form allows the radiologist to view and make changes to patient information. When the radiologist is finished interacting with radiologist Online Form 1402, the radiologist can select a save button 1406 to save the data from the form. Selecting save button 1406 can also push the data from radiologist Online Form 1402 to a variety of entities, including dispatcher interface 1100 and an external MIS.

Speech capture interface 1404 is configured to display audio input as graphical text. In one implementation, the radiologist can examine the images from image interface 1400 and provide a verbal analysis of the images. An application associated with speech capture interface 1404 can receive the verbal analysis (e.g., as an audio file) and convert the audio input into graphical text for display on the interface. Workflow tool 112 is configured to automatically capture data from other data sources, such as an Online Form, a worklist interface (e.g., dispatcher interface 1100 or a radiologist interface 1300), an external MIS, and so on, and populate speech capture interface 1404 with the data. As illustrated here, speech capture interface has been populated by workflow tool 112 with information from tech Online Form 1000 and dispatcher Online Form 1200 (i.e., the text displayed in the "Clinical Information" field). The radiologist can then enter further findings and patient data into speech capture interface 1404 via spoken input. When the radiologist is finished interacting with speech capture interface 1404, the radiologist can select a sign button 1408. In one implementation, selecting sign button 1408 indicates that the radiologist has completed his or her analysis of the medical images from image interface 1400.

Figure 15:
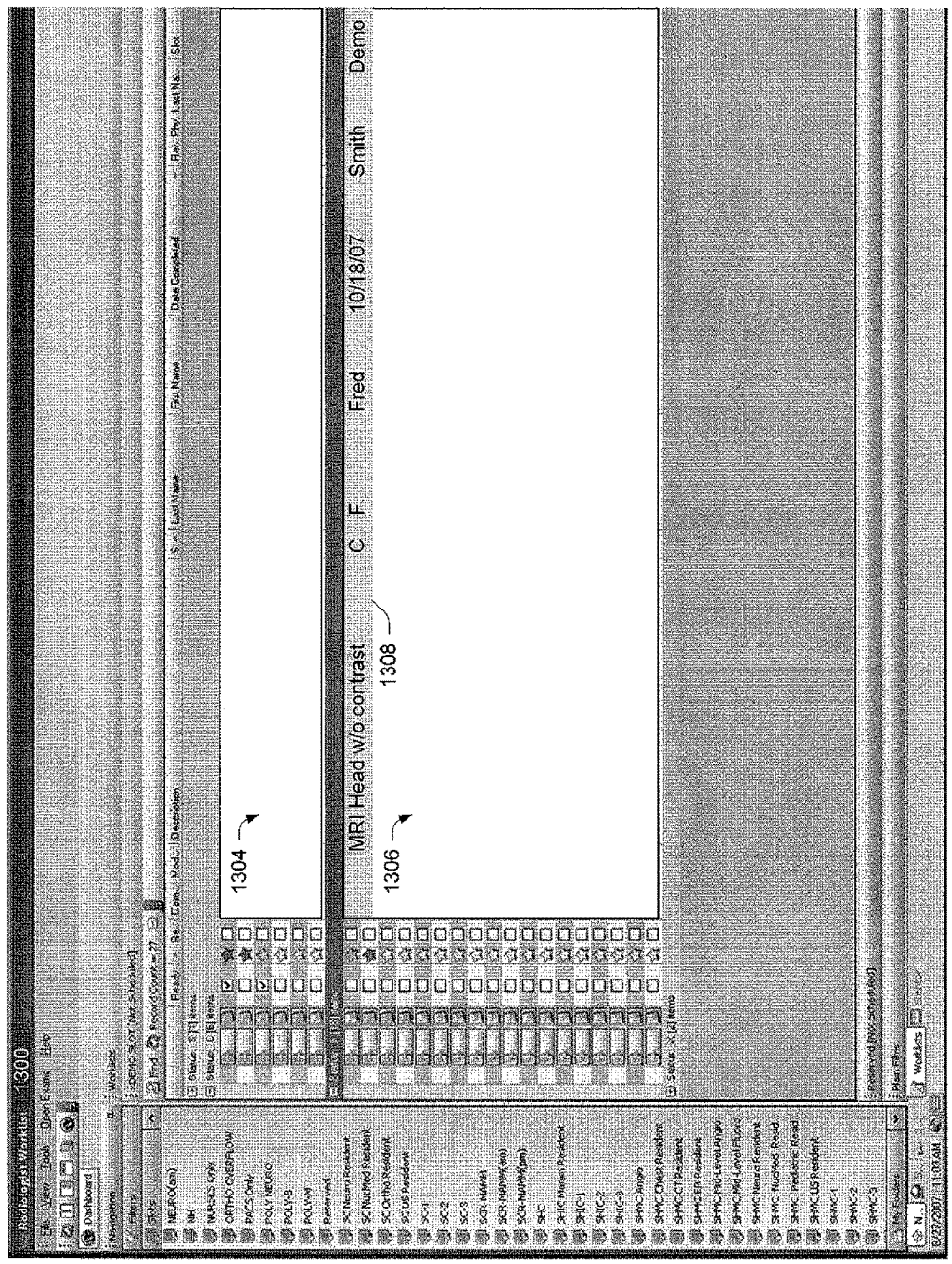
FIG. 15 illustrates one example of a radiologist worklist interface in accordance with one or more embodiments.

FIG. 15 illustrates an updated version of radiologist interface 1300, in accordance with one or more embodiments. In this version, task record 1308 has been moved from completed task region 1304 to finished task region 1306, indicating that the radiologist has finished his or her analysis of the images associated with task record 1308. In one implementation, marking task record 1308 as finished automatically pushes the task record to another entity, such as a dispatcher or other medical worker. Thus, the task record can be pushed to a referring physician or a specialist, indicating to these personnel that the analysis of the medical images has been completed and further tasks in the medical workflow associated with task record 1308 can be completed.

PROCESS EXAMPLES

FIGS. 16-20 illustrate several processes that can implement the described methods and techniques, in accordance with one or more embodiments. These processes, along with any other processes discussed herein, may be implemented in any suitable hardware, software, firmware, or combination thereof; in the case of software and firmware, these processes and flow diagrams represent sets of operations implemented as computer-executable instructions stored in computer-readable media and executable by one or more processors. Computer-readable media can include storage media, communication media, and/or any other suitable type of media. The order in which particular acts occur in these processes is not intended to be limiting and the particular processes and acts can be combined and performed in a variety of manners without departing from the spirit and scope of the claimed embodiments.

Figure 16:
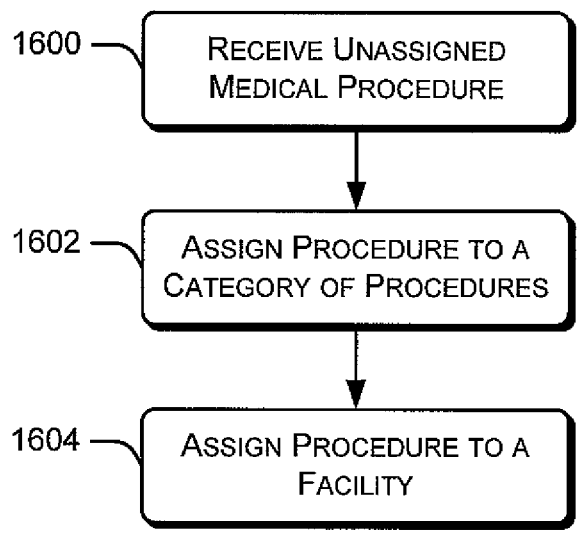
FIG. 16 is a flow diagram of a process for assigning medical procedures to categories in accordance with one or more embodiments.

FIG. 16 illustrates one process for assigning a medical procedure to a particular slot. At 1600, a medical worker enters a request for some type of medical procedure. In one example, act 1600 can include an MRI technician requesting an analysis of MRI images via an Online Form. At 1602, the unassigned procedure is assigned to a general category of procedures. Continuing the example above, this can include assigning the assignment of the MRI images to a particular medical category (e.g., "general orthopedics"). At 1604, the procedure is then assigned to a particular facility that can complete the procedure. This process can be implemented in whole or in part using folder sets, discussed above. A particular folder set can represent general MRI-related procedures, a folder within the folder set can represent specific MRI procedures ("MRI Orthopedic"), and an instance of a medical procedure can be placed as an item in the folder. Thus, to locate the instance, one could locate the MRI folder set, the MRI Orthopedic folder, and traverse the items in the folder to locate the instance of the medical procedure.

Figure 17:
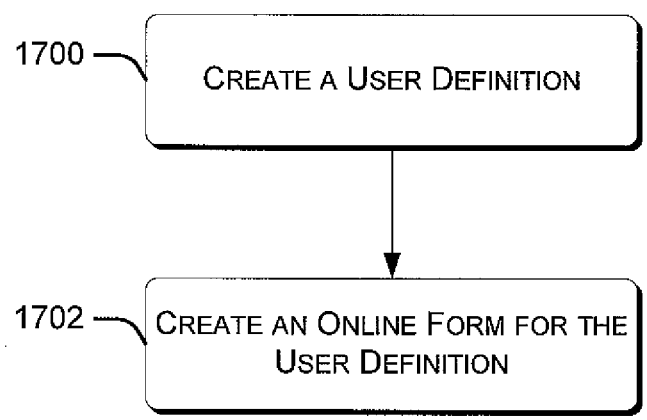
FIG. 17 is a flow diagram of a process for creating an Online Form in accordance with one or more embodiments.

FIG. 17 illustrates one example of a process for creating an Online Form for particular user roles in a medical procedure and/or medical workflow. At 1700, a user definition is created. A user definition can be based on a user's professional role, such as a medical technologist, a physician, a medical workflow dispatcher, and so on. The user definition can also include security clearances, security tokens, and other aspects related to user permissions. In some instances, the user definition can be customizable by specific users, allowing users to define the particular data set that the user can view and interact with via an Online Form. At 1702, an Online Form is created based on the user definition. The Online Form can be stored at any suitable location, including forms archive 316.

Figure 18:
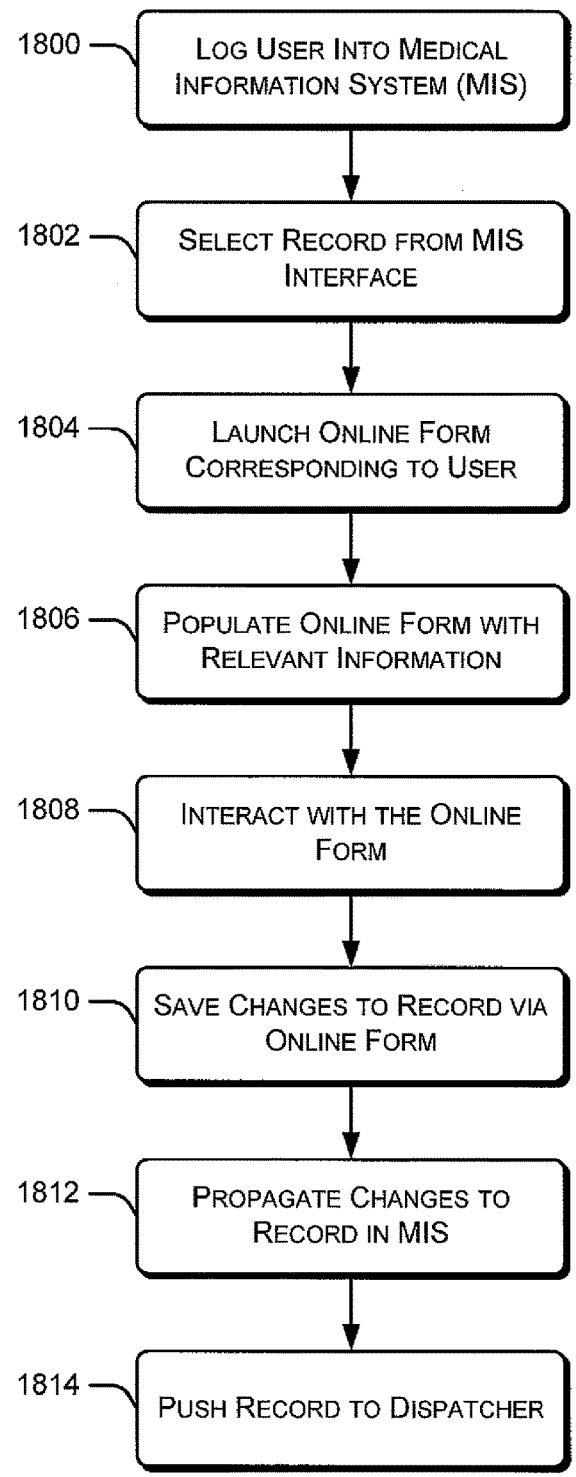
FIG. 18 is a flow diagram of a process for interacting with a medical workflow with a workflow tool in accordance with one or more embodiments.

FIG. 18 illustrates one example of a process that implements certain aspects of workflow tool 112. At 1800, a user logs into an MIS. At 1802, the user selects a medical record from the MIS to interact with. The medical record can include individual patients and/or medical workflows. At 1804, the workflow tool detects the selection of the medical record and launches an Online Form that corresponds to the particular user. At 1806, the Online Form is automatically populated with relevant medical information associated with the medical record. The information can be extracted from the MIS or any other suitable data source.

At 1808, the user interacts with the Online Form by entering new data and/or editing the data that has been automatically populated into the form. Interaction with the Online Form can include linking a medical image to the form, such as a patient MRI image. At 1810, the user saves any changes made to the medical record via the Online Form. At 1812, any changes made to the medical record via the Online Form at propagated to the medical record stored in the MIS. At 1814, the medical record is pushed to a dispatcher as a new medical task, a new medical workflow, or an update to a medical task or workflow that currently exists at the dispatcher.

Figure 19:
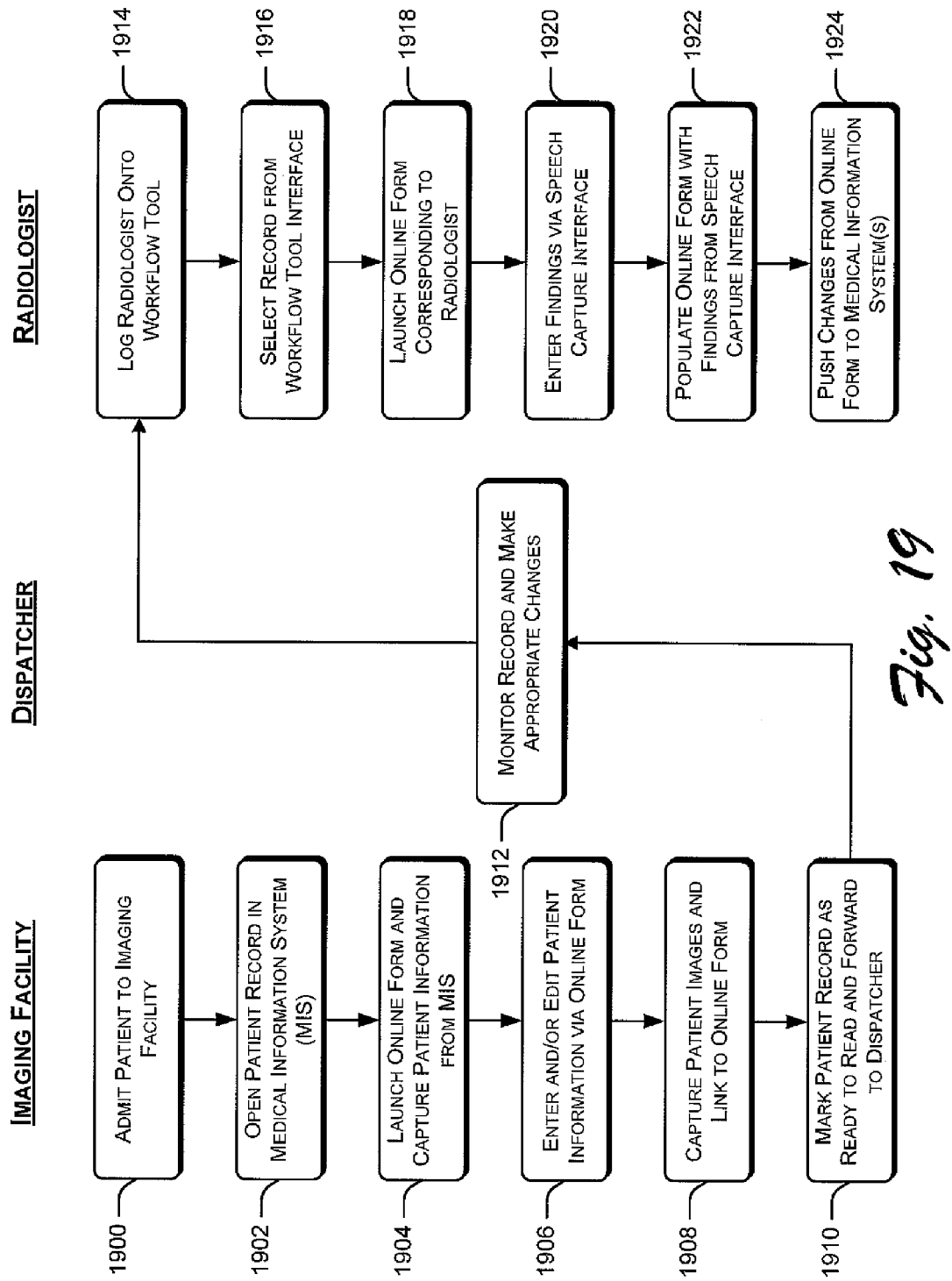
FIG. 19 is a flow diagram of a process for interacting with a medical workflow with a workflow tool in accordance with one or more embodiments.

FIG. 19 illustrates one implementation of a process that can implement aspects of the processes and techniques discussed herein. For purposes of this example, the process is divided into acts that can occur at a medical imaging facility, at a dispatcher, and at a radiologist facility. At 1900, a patient is admitted to an imaging facility to undergo some type of imaging process (e.g., MRI, CT, ultrasound, and so on). At 1902, a medical worker at the imaging facility, as part of a patient intake process, opens a medical record associated with the patient via an MIS. The medical record may be a preexisting record, or the medical worker may create a new medical record via the MIS. At 1904, an Online Form configured for the medical worker is launched by a workflow tool that wraps the MIS, and the form is automatically populated with information about the patient. At 1906, the medical worker enters patient information into the Online Form and can edit the information that was automatically populated into the form. At 1908, medical images of the patient are captured and are linked to the Online Form. At 1910, the patient's medical record is marked as ready to read (i.e., there are medical images ready to be interpreted) and the record is forwarded to a dispatcher as a new medical task, a new medical workflow, or as changes to an existing medical task and/or medical workflow. As part of act 1910, any changes to the patient's medical record can be saved and propagated to external instances of the medical record (e.g., at an external MIS and/or a dispatcher interface).

At 1912, a dispatcher monitors the medical record and makes any appropriate changes to the record. To edit the record, the dispatcher can open the record and launch an Online Form configured for the dispatcher.

At 1914, a radiologist logs onto the workflow tool. At 1916, the radiologist selects a record to interact with from the workflow tool interface. In this example, the record corresponds to the patient medical record discussed in the previous acts of this process. At 1918, a radiologist Online Form is launched in response to the radiologist's selection of the record from the workflow tool interface. As discussed earlier, other interfaces can also be launched in response to the radiologist's selection of a medical record, including a speech capture interface, a medical image interface, and so on. At 1920, the radiologist views the medical images and enters any interpretation of the images via the speech capture interface. At 1922, the workflow tool automatically captures any data entered via the speech capture interface and populates the radiologist Online Form with the data. At 1924, changes made to the medical record (e.g., findings by the radiologist and/or data populated into the Online Form) are saved and pushed to an external instance of the medical record that exists in an external MIS.

Figure 20:
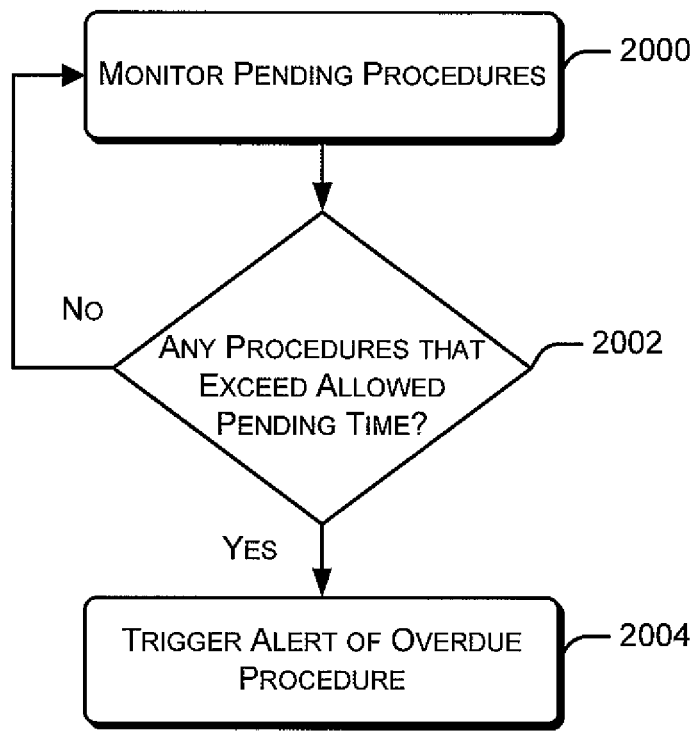
FIG. 20 is a flow diagram of a process for monitoring pending medical procedures in accordance with one or more embodiments.

FIG. 20 illustrates a process that can monitor pending medical procedures and/or workflows. The process can be implemented at a dispatcher via a dispatcher interface, and can utilize aspects of the discussed techniques and implementations. At 2000, pending medical procedures and/or workflows are monitored. At 2002, it is determined if any pending medical procedures have exceeded or are about to meet or exceed an allowed pending time. For example, pending medical procedures can be assigned a certain allowed pending time. In one implementation, a medical procedure can be labeled as an "emergency procedure" or stat, and be given a finite allowed pending time (e.g., 10 minutes), within which the procedure must be completed. If the dispatcher's permissions allows, the dispatcher can view a pending medical procedure and elevate the procedure to emergency status or demote the procedure from emergency status to non-emergency status.

If it is determined that no pending procedures have exceeded an allowed pending time, the process returns to act 2000 and continues monitoring pending procedures. If it is determined that a procedure is approaching an allowed pending time, or has met or exceeded an allowed pending time, at 2004 an alert is triggered that an exam is overdue or is about to become overdue. In some implementations, a dispatcher can reassign an overdue procedure to another entity (e.g., a medical worker or medical facility) that is able to perform the procedure in a timely manner. In one example, a dispatcher can determine if an entity is able to perform a procedure in a timely manner by examining a workflow queue associated with the entity. If the workflow queue indicates that the entity is performing its assigned medical tasks within a prescribed time limit and that the workflow queue has room for more tasks, the dispatcher can reassign medical tasks to the entity. In other implementations, the procedure can be automatically reassigned by the workflow tool in response to the alert.

Workflow Analytics

The following section presents a discussion of workflow analytics techniques that can be used to analyze medical workflows and generate reports based on the analysis. These techniques can be helpful to various medical workers and administrators in maximizing the efficiency of various medical workflows and processes. These techniques can be implemented using workflow analytics module 220, discussed above.

Figure 21:
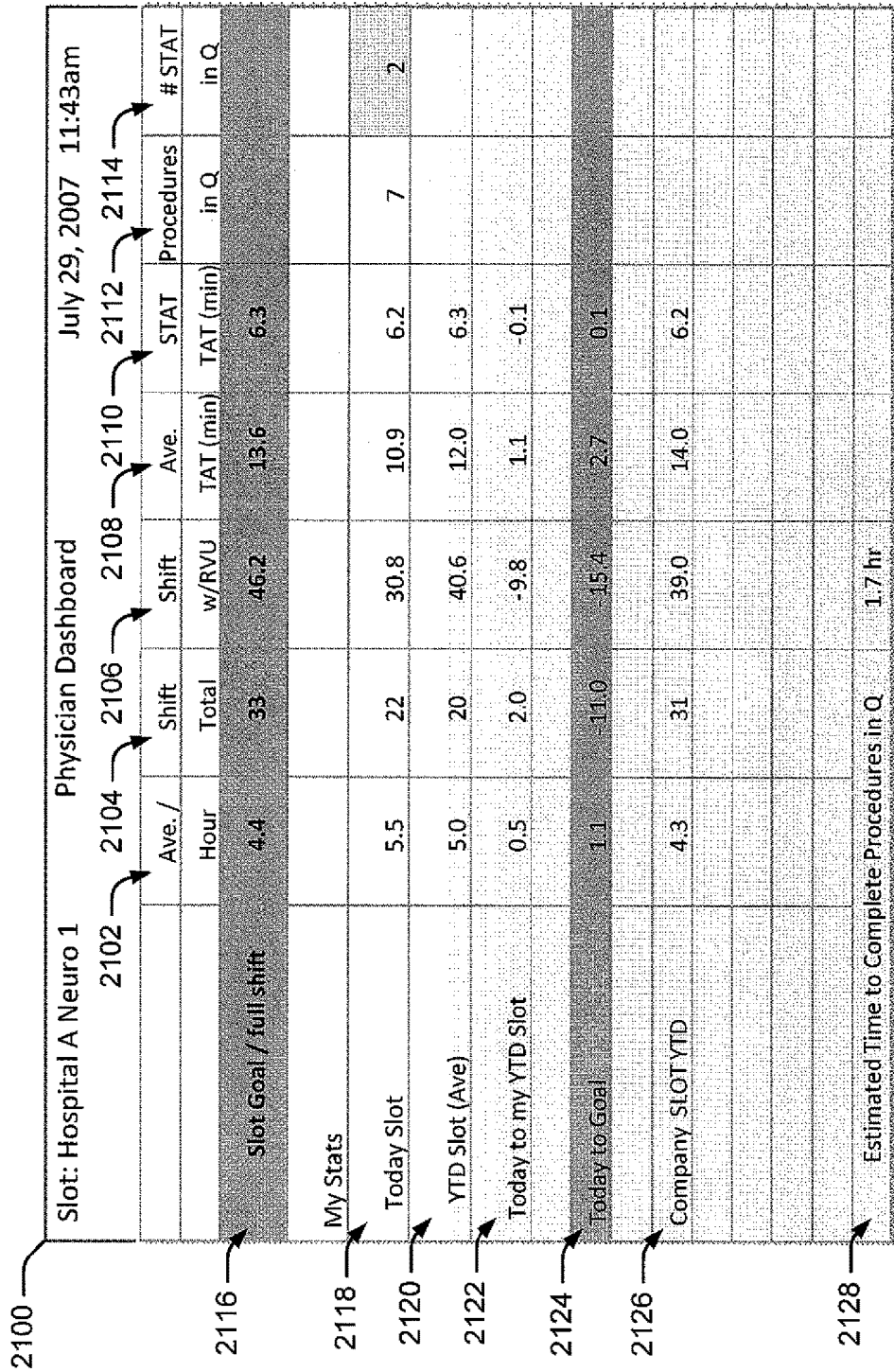
FIG. 21 illustrates one example of a physician dashboard for analyzing physician workflow in accordance with one or more embodiments.

FIG. 21 illustrates one example of a physician dashboard 2100, in accordance with one or more embodiments. A physician is used for purposes of example only, and other dashboards can be configured for a variety of different medical personnel without departing from the spirit and scope of the claimed embodiments. Physician dashboard 2100 includes several rows and columns of data that provide statistics concerning a particular physician's workflow. These rows and columns are described below:

Columns:

Column 2102 shows the average number of particular medical procedures performed per hour.

Column 2104 shows the total number of medical procedures performed during a particular work shift.

Column 2106 shows the total number of relative value units (RVUs) accumulated for a particular shift.

Column 2108 shows an average turnaround time (TAT) in minutes for a particular group of medical procedures.

Column 2110 shows an average turnaround time (TAT) in minutes for a stat group of medical procedures (i.e., medical procedures that must be performed immediately).

Column 2112 shows a number of medical procedures currently in a procedure queue (i.e., the number of procedures currently waiting to be started and/or completed).

Column 2114 shows a number of stat procedures that currently in the procedure queue.

Rows:

Row 2116 shows a physician's shift goal for each of the column values.

Row 2118 shows the values for each column for a particular physician day.

Row 2120 shows the year-to-date daily average for the physician for each column value.

Row 2122 compares the column values for the particular physician day with the year-to-date daily averages.

Row 2124 shows a comparison of the physician's actual current production compared to the shift goal specified in row 2116.

Row 2126 shows the average year-to-date values for Hospital A for each of the column values.

Row 2128 shows an estimated time for the physician to complete the procedures currently in the procedure queue.

FIG. 22 illustrates a medical facility dashboard 2200 that provides statistics for specific medical facilities, in accordance with one or more embodiments. This example is for a "Hospital A Radiology" department; however, any medical facility and any department can utilize a similar dashboard. The numbers and statistics provided in medical facility dashboard 2200 can be compiled from a number of sources, including physician dashboard 2100. Medical facility dashboard 2200 includes several rows and columns of data that provide statistics concerning a particular medical facility's workflow. These rows and columns are described below:

Columns:

Column 2202 shows an average turnaround time (TAT) for medical procedures within this facility.

Column 2204 shows an average year-to-date TAT for medical procedures at this facility.

Column 2206 shows the variance between the values in column 2202 and column 2204.

Column 2208 shows a number of medical procedures currently in a procedure queue.

Column 2210 shows a number of stat procedures currently in the procedure queue.

Rows:

Row 2212 shows the column values for preliminary reports for medical procedures in an emergency department.

Row 2214 shows the column values for final reports for medical procedures in the emergency department.

Row 2216 shows column values for preliminary reports for medical procedures in other non-emergency departments.

Row 2218 shows column values for final reports for medical procedures in other non-emergency departments.

Row 2220 shows the total number of medical procedures completed for a particular day.

Row 2222 shows the average number of medical procedures completed by this facility for the year-to-date.

Row 2224 shows any variance between the value in row 2220 and the value in row 2222.

Row 2226 shows a year-to-date cumulative variance value.

Figure 23:
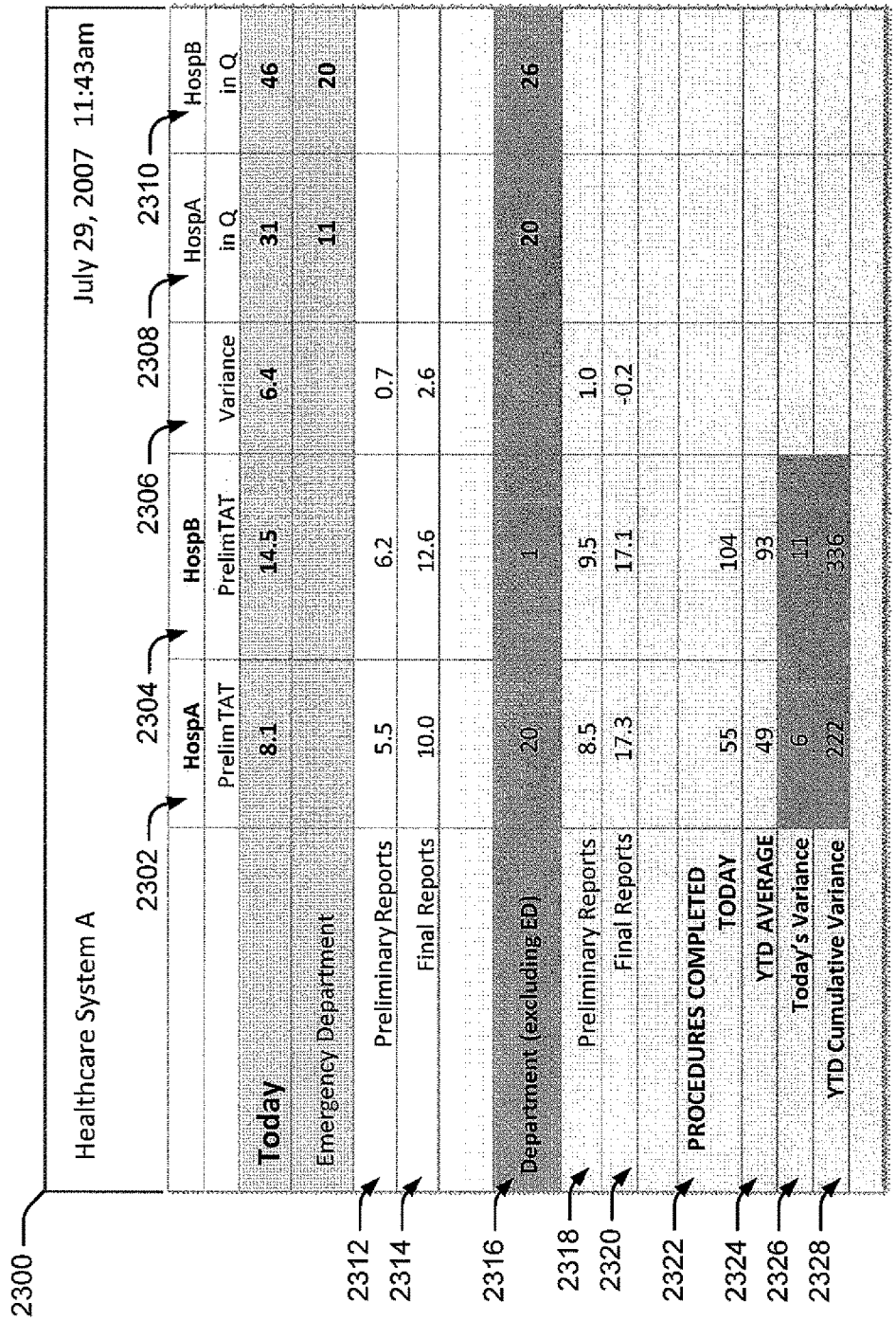
FIG. 23 illustrates one example of a healthcare system dashboard for analyzing healthcare system workflow in accordance with one or more embodiments.

FIG. 23 illustrates a healthcare system dashboard 2300 that can be used to track the performance of one or more facilities within a particular healthcare system, in accordance with one or more embodiments. The performance can be quantified in terms of a number of medical procedures performed over a given time period. Healthcare system dashboard 2300 includes several rows and columns of data that provide statistics concerning a particular healthcare system's workflow. These rows and columns are described below:

Columns:

Column 2302 shows a preliminary turnaround time (TAT) for medical procedures in Hospital A.

Column 2304 shows a preliminary TAT for medical procedures in Hospital B.

Column 2306 shows that variance between the values in column 2302 and the values in column 2304.

Column 2308 shows the number of medical procedures in a procedure queue for Hospital A.

Column 2310 shows the number of medical procedures in a procedure queue for Hospital B.

Rows:

Row 2312 shows the column values for medical procedure preliminary reports in the emergency departments of the listed facilities (i.e., Hospital A and Hospital B).

Row 2314 shows the column values for medical procedure final reports in the emergency departments of the listed facilities.

Row 2316 shows the column values for other departments besides the emergency departments of the listed facilities.

Row 2318 shows the column values for preliminary reports in other departments besides the emergency departments of the listed facilities.

Row 2320 shows the column values for final reports in other departments besides the emergency departments of the listed facilities.

Row 2322 shows the number of medical procedures completed for the reporting day in each of the listed facilities.

Row 2324 shows the year-to-date daily average of the number of procedures completed in each of the listed facilities.

Row 2326 shows the reporting day's variance from the year-to-date daily average.

Row 2328 shows the year-to-date cumulate variance.

Figure 24:
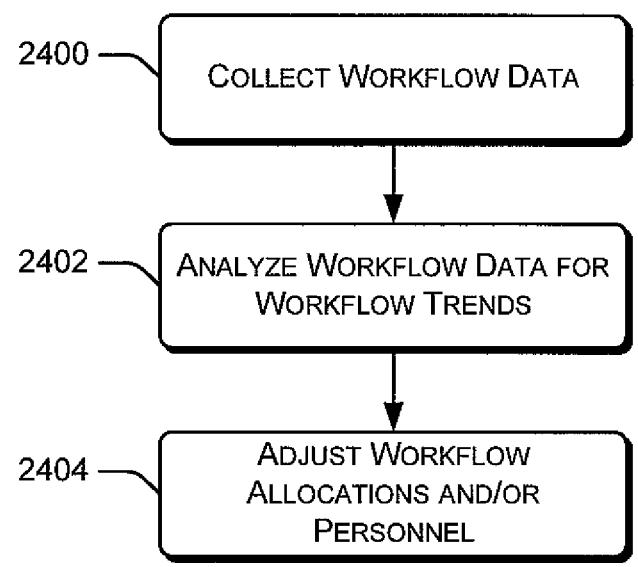
FIG. 24 is a flow diagram of a process for optimizing medical workflow in accordance with one or more embodiments.

FIG. 24 illustrates one example of a process that can utilize data from the dashboards discussed above, in accordance with one or more embodiments. At 2400, medical workflow data is collected. In one implementation, act 2400 includes collecting data from one or more of the dashboards. At 2402, statistical analysis of the workflow data is performed. The statistical analysis can be used to measure medical throughput of specific medical professionals, medical facilities, and/or medical systems. At 2404, workflow allocations and/or personnel adjustments are made to maximize the throughput or efficiency of personnel, facilities, and/or systems. This can include reassigning medical procedures from personnel or facilities that are running behind schedule or are not meeting expected turnaround times to personnel or facilities that have the capacity to handle an increased workload (e.g., more medical procedures).

Resource Scheduling

The following section presents a discussion of medical resource scheduling. In some examples, medical resources can refer to human medical resources, such as physicians, technicians, nurses, and so on. Using the describes processes and techniques, medical resources can be intelligently scheduled to account for a variety of medical resource attributes, such as the medical credentials of a particular medical worker, the capabilities of a particular medical facility, the scheduling constraints of medical personnel, and so on. In some implementations, resource scheduler 215 can be utilized to implement the described processes, techniques, and interfaces.

Figure 25:
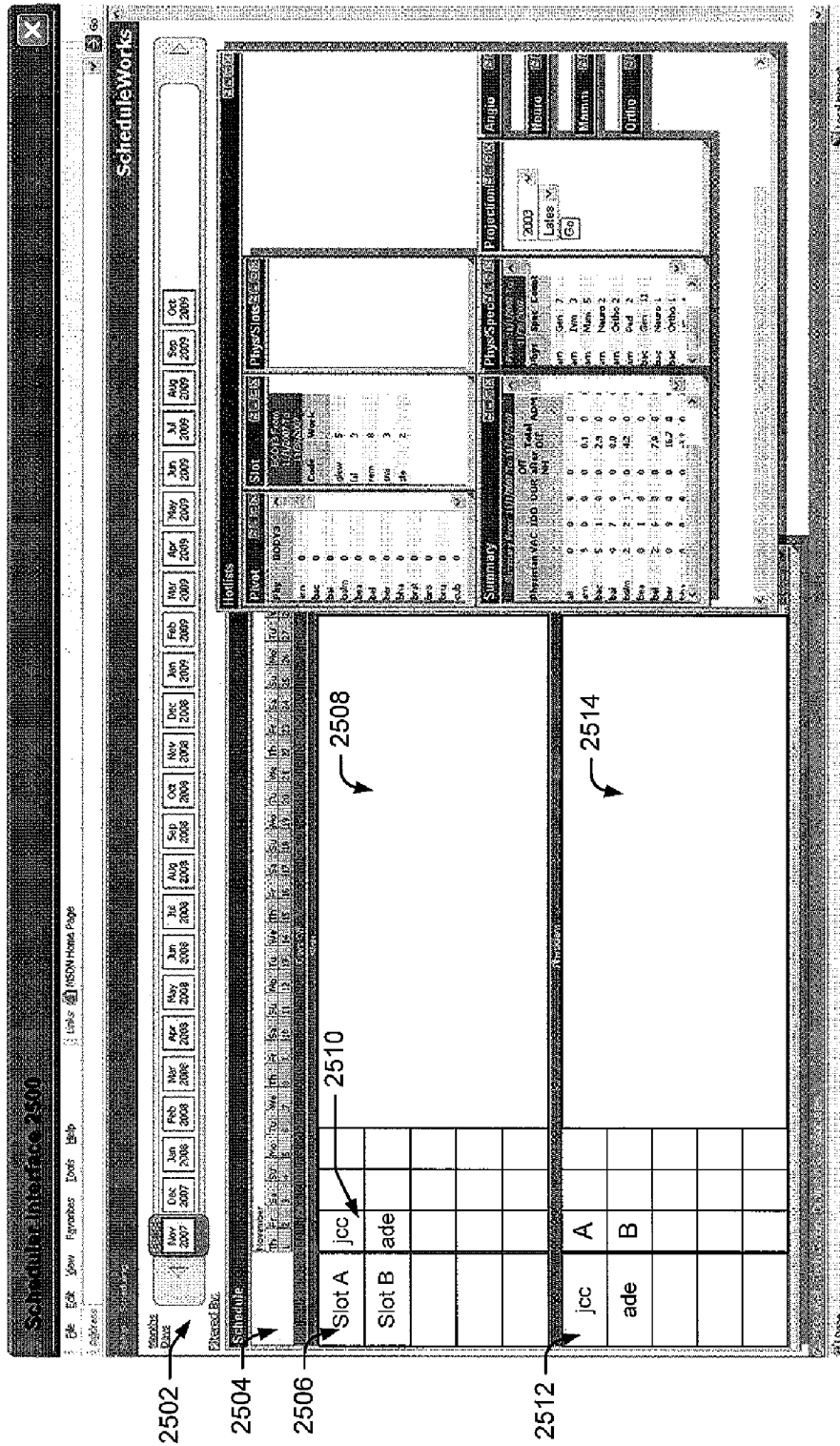
FIG. 25 illustrates one example of a scheduler interface in accordance with one or more embodiments.

FIG. 25 illustrates one example of a scheduler interface 2500 that can be used to schedule a variety of medical resources. In operation, scheduler interface 2500 can be implemented by any suitable medical worker, such as a dispatcher or a medical scheduler. Scheduler interface 2500 includes a date field 2502 that allows a user to select a particular date and view medical resources scheduled for the date in the scheduler interface. The date selected in date field 2502 can be broken down into individual days via a day field 2504. A slot field 2506 displays slots that can be scheduled for the days displayed in day field 2504. A medical resource field 2508 displays medical resources that have been scheduled for a particular slot from slot field 2506 and for a particular day from day field 2504. Thus, an assignment cell 2510 indicates that a physician with the initials "jcc" is scheduled for slot A on a particular day.

Scheduler interface 2500 can also display schedules in terms of particular medical resources. Thus, a medical resource field 2512 displays medical resources that can be employed to complete medical tasks associated with a particular slot and/or medical workflow. A slot schedule field 2514 displays slots that have been associated with particular medical resources from medical resource field 2512. As shown, medical resource "jcc" is scheduled for slot A on a particular day and medical resource "ade" is scheduled for slot B on that day.

Figure 26:
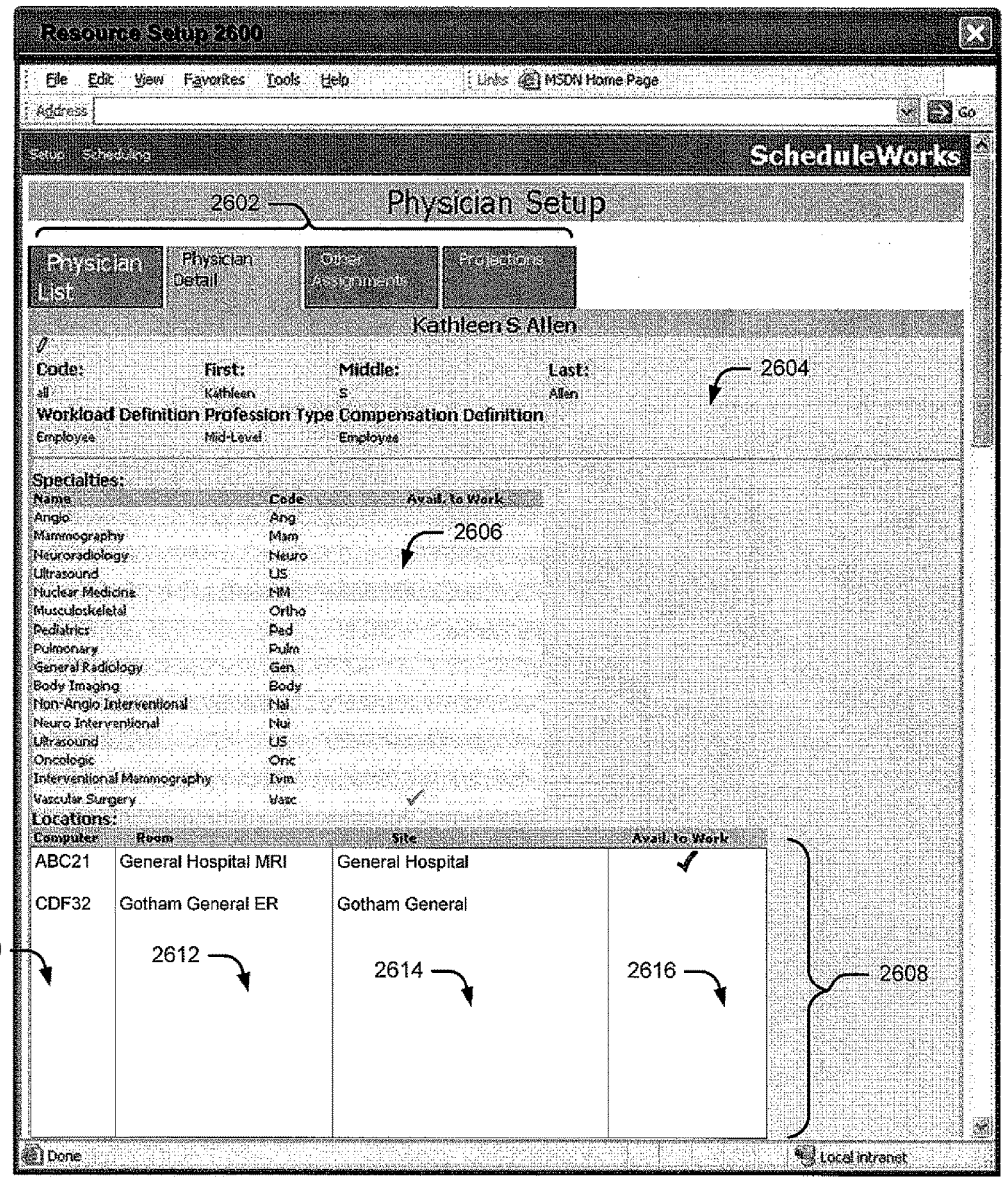
FIG. 26 illustrates one example of a resource setup interface in accordance with one or more embodiments.

FIG. 26 illustrates one example of a resource setup interface 2600 that can be used to define a medical resource in workflow tool 112. A physician is used here for purposes of example only, and any suitable medical worker or medical resource can be defined using resource setup interface 2600. In some implementations, resource setup interface 2600 can be displayed in response to the selection of a resource in one of the user interfaces discussed herein.

Illustrated at 2602 are a variety of tabs that can switch the setup view in resource setup interface 2600. A physician list tab can shown a list of physicians that are part of the workflow tool system. A physician detail tab displays several fields that include details about a particular physician. As part of a physician detail view, an overview field 2604 includes a physician name and human resource details about the physician. A specialties field 2606 lists a variety of medical specialties that can be associated with a particular physician. As part of defining a physician (or other medical resource), one or more of the listed medical specialties can be selected, indicating that the particular resource being defined is available to complete medical tasks within the selected medical specialty. In this example, the physician "Kathleen S. Allen" is available to participate in medical tasks that include the specialty of vascular surgery, as indicated by the check mark next to vascular surgery in the "available to work" column.

Resource setup interface 2600 also includes a location region 2608, which contains several fields, such as a computer field 2610, a room field 2612, a site field 2614, and an available field 2616. Location region 2608 can list a variety of medical locations, such as hospitals, imaging facilities, medical equipment, and so on, that are available to complete medical tasks as part of a medical workflow. A medical location can refer to physical and/or virtual locations. When a medical resource is defined using resource setup interface 2600, the medical resource can be associated with particular medical locations, thus indicating that the medical resource is available to complete tasks at the particular medical locations.

Computer field 2610 can list a variety of devices, such as client terminals, control terminals, servers, and so on. Room field 2612 can list rooms at particular locations, such as imaging rooms, reading rooms, operating rooms, and so on. Site field 2614 can list sites associated with rooms and devices in the previously mentioned fields. Available field 2616 can contain indicators that the resource defined in resource setup interface 2600 is available to work at the particular device, room, and/or site indicated in the other fields in location region 2608. In this example, Dr. Allen is available to work in the General Hospital MRI room, as indicated by the check mark in available field 2616, but not at the Gotham General ER, as indicated by the absence of a check mark next to that location.

Figure 27:
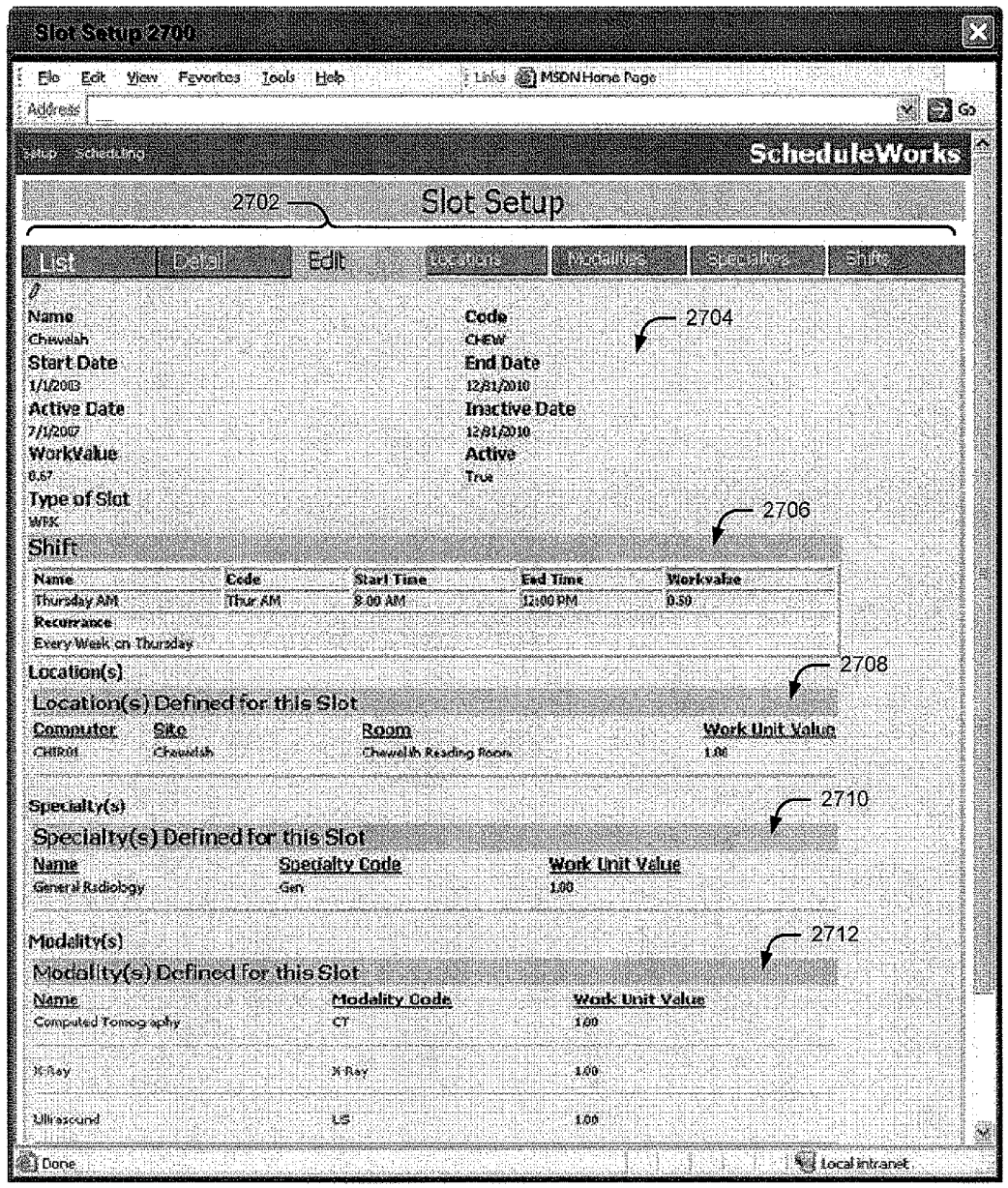
FIG. 27 illustrates one example of a slot setup interface in accordance with one or more embodiments.

FIG. 27 illustrates a slot setup interface 2700 that enables a user to set the parameters that define a slot. In some implementations, slot setup interface 2700 can be displayed in response to a user selection of a slot in one of the user interfaces discussed herein.

Slot setup interface 2700 includes several subject tabs, as shown at 2702. The subject tabs allow different aspects of a slot to be viewed and configured. In this example the edit tab is selected, which enables a user to edit certain aspects of a slot. A slot details region 2704 lists a variety of slot details, such as the slot name, dates associated with the slot, slot codes, and so on. In this example, the slot is named "Chewelah", has a start date of Jan. 1, 2003, an active date of Jul. 1, 2007, and so on as illustrated.

A shift details region 2706 allows the details of particular shifts associated with a slot to be specified. As illustrated in this example, shift details include a shift name, a shift start time, a shift end time, and so on. A location region 2708 lists one or more locations at which the medical tasks associated with the slot can be completed. A specialty region 2710 enables particular medical specialties to be associated with the slot being viewed. In this example, the "Chewelah" slot includes the "General Radiology" medical specialty.

A modality field 2712 lists a variety of medical modalities that can be associated with a particular slot. Using modality field 2712, modalities can be added, deleted, or modified in each slot. In this example, imaging modalities are listed, such as computed tomography, x-ray, ultrasound, and so on.

Figure 28:
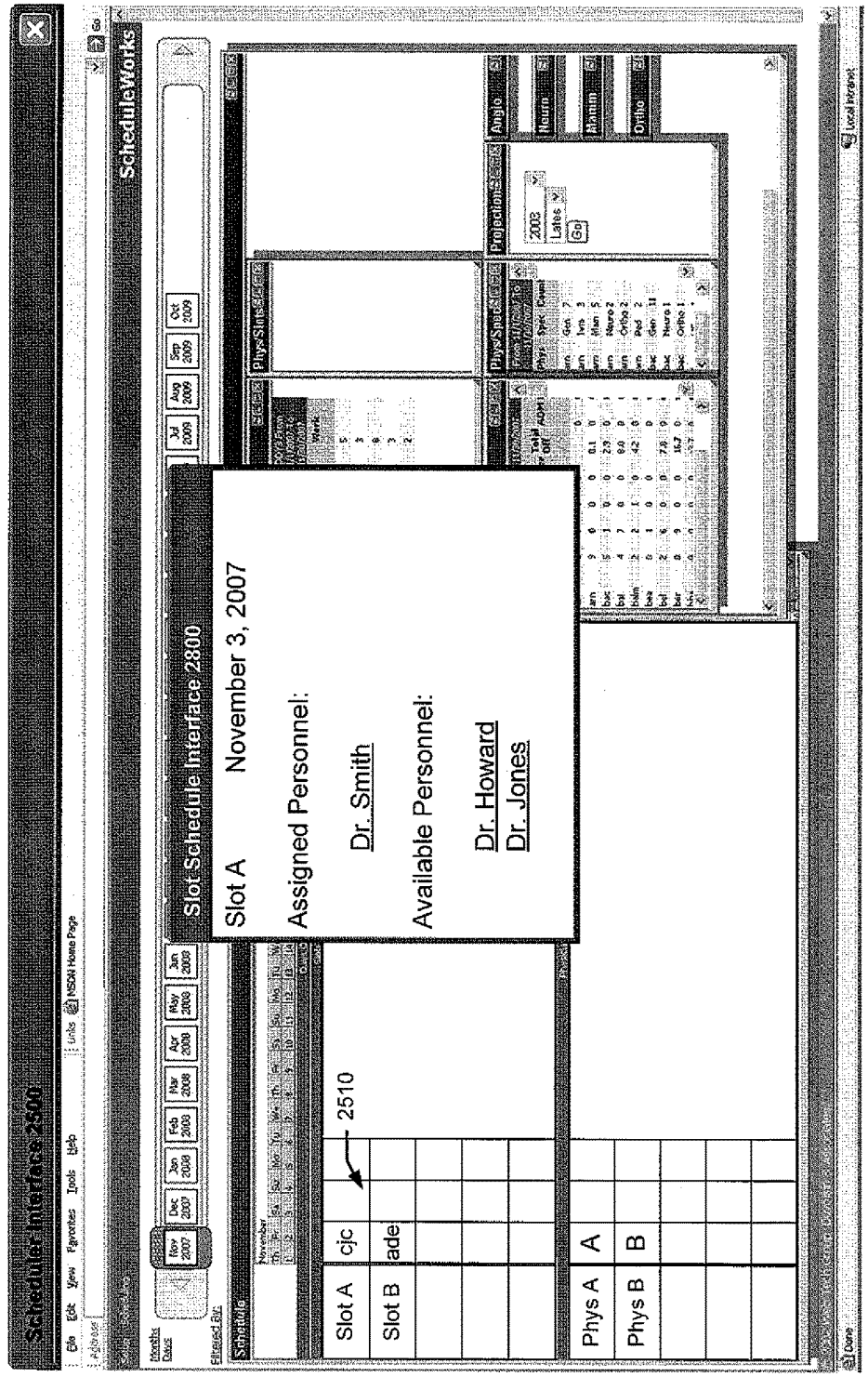
FIG. 28 illustrates one example of a slot schedule interface in accordance with one or more embodiments.

FIG. 28 illustrates one example of a slot schedule interface 2800 that can be used to set one or more scheduling parameters for a particular slot. Slot schedule interface 2800 is discussed with reference to scheduler interface 2500 and, in some implementations, can be invoked by selecting a particular slot and a particular date and/or time. In this example, slot schedule interface 2800 is displayed in response to the selection of assignment cell 2510. As illustrated, slot schedule interface 2800 displays slot parameters for "Slot A" on Nov. 3, 2007. Slot schedule interface enables resources to be assigned to particular slots, and displays these resources when the interface is invoked. In this example, Dr. Smith has been assigned to this particular slot, and Dr. Howard and Dr. Jones are available to work this slot. Thus, in one example, a user could assign Dr. Howard and/or Dr. Jones to this slot, and this assignment would be reflected in slot schedule interface 2800.

Figure 29:
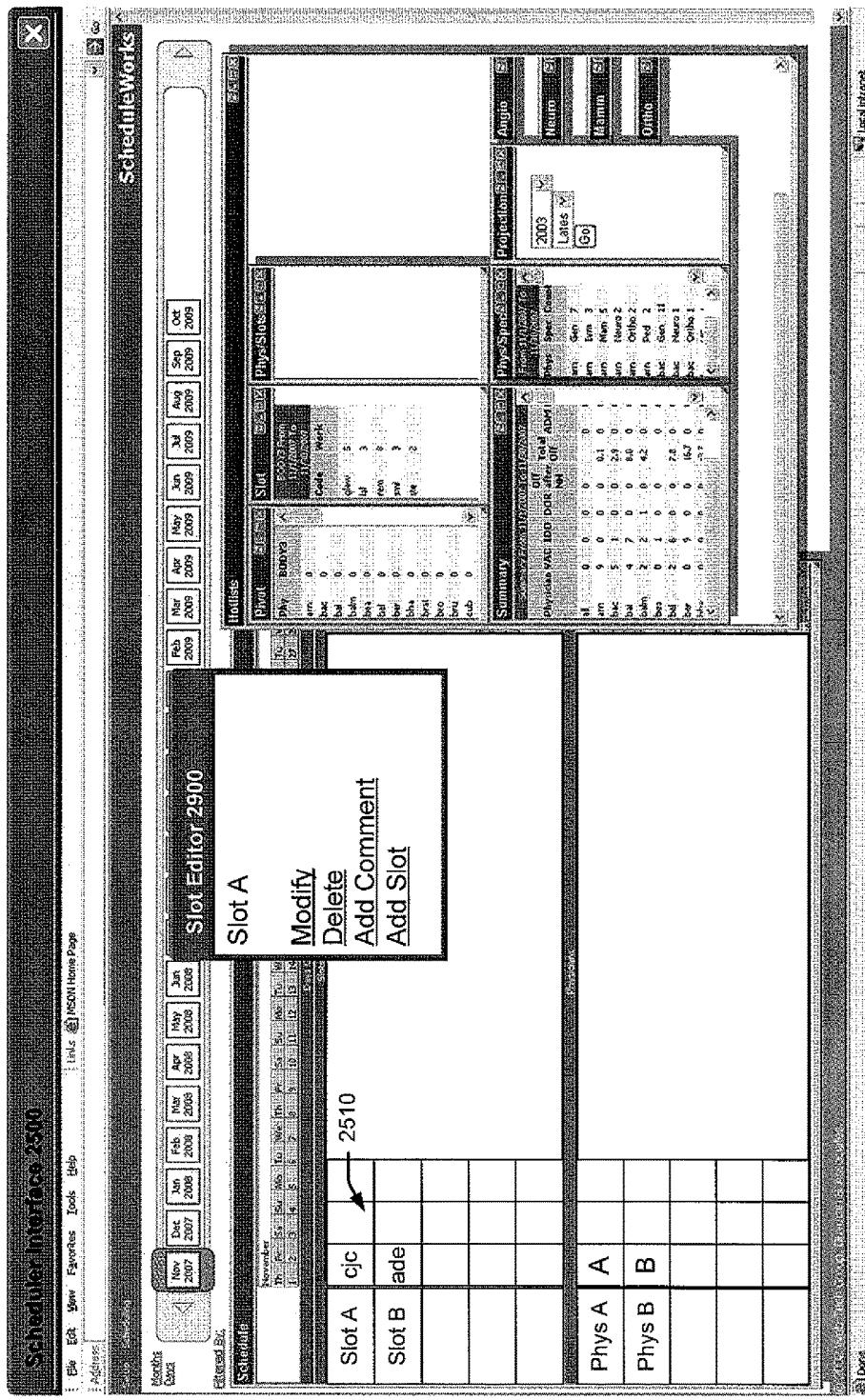
FIG. 29 illustrates one example of a slot editor interface in accordance with one or more embodiments.

FIG. 29 illustrates one example of a slot editor 2900 that enables slot editing functions to be performed. In this example, slot editor 2900 is invoked by selecting a particular slot and time/date for the slot, such as assignment cell 2510. In this example, slot editor 2900 lists the editing functions "modify", "delete", "add comment", and "add slot". These are simply examples, and any suitable editing function can be invoked using slot editor 2900. The listed editing functions can include hotlinks that, when selected, automatically invoke an interface that can enable a user to complete the selected function.

Figure 30:
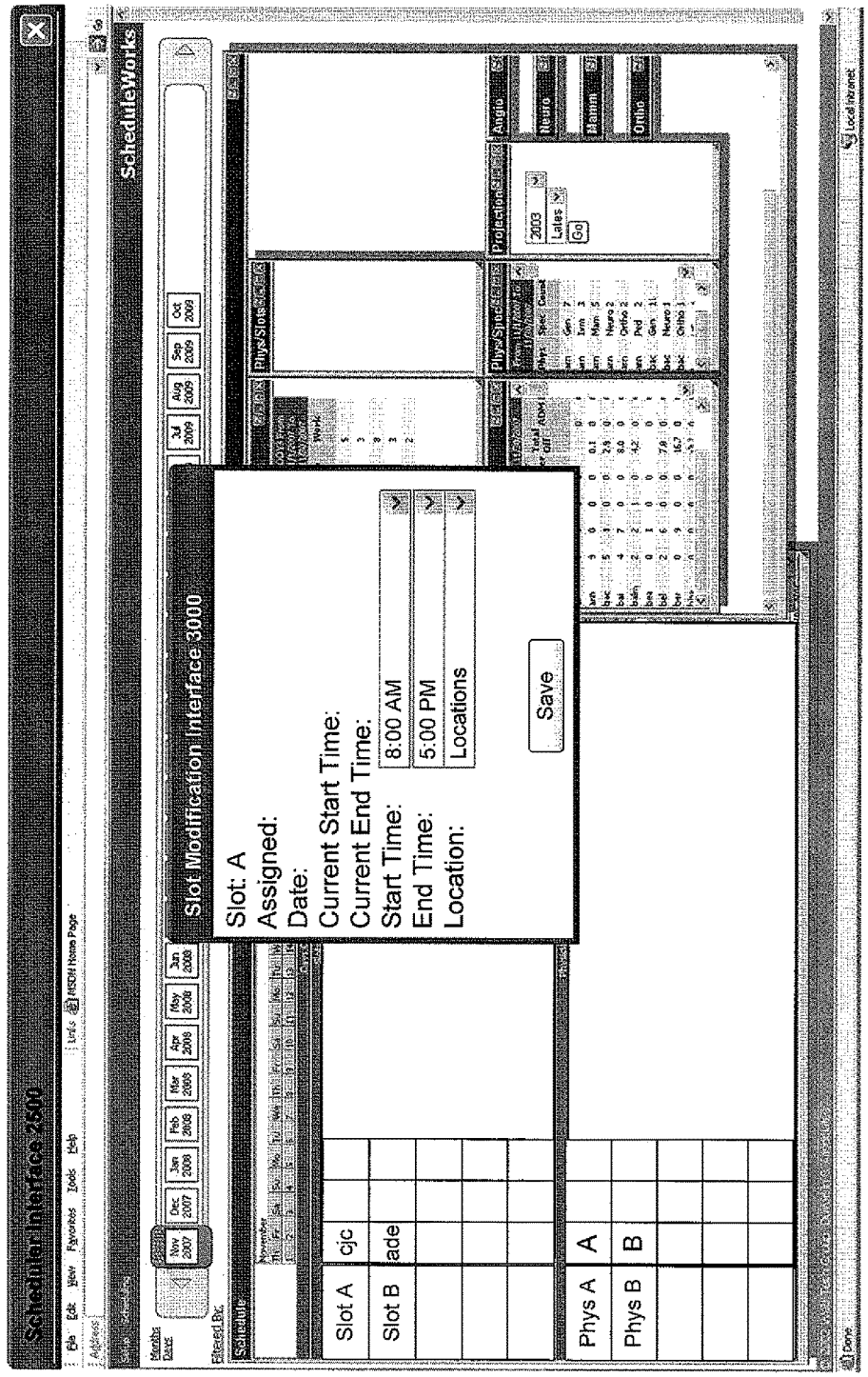
FIG. 30 illustrates one example of a slot modification interface in accordance with one or more embodiments.

FIG. 30 illustrates one example of a slot modification interface 3000 that enables a user to modify certain slot parameters. Slot modification interface 3000 is discussed in reference to scheduler interface 2500 and, in some implementations, can be invoked by selecting the "modify" function in slot editor 2900. In this example, slot modification interface 3000 enables a user to modify Slot A. The interface can display a list of medical resources assigned to the slot, a date for the slot, and start time and finish time for the slot. Slot modification interface 3000 can also include a variety of menus that enable a user to alter slot parameters. In this example, the interface includes drop-down menus that enable a user to select a start time, an end time, and locations for the slot. These parameters are presented for purposes of example only, and a slot modification interface can be configured to modify any suitable slot parameter using any suitable type of modification menu.

Using these various scheduling interfaces enables users of workflow tool 112 to schedule a variety of medical resources over an extended period of time. Resource scheduler 215 can interact with workflow dispatcher 216 to ensure that scheduling conflicts do not occur. Resource scheduling rules can be created and enforced over an entire workflow system. For example, a physician profile that is created via resource setup interface 2600 can be associated with a set of medical credentials. A particular physician associated with the physician profile may be qualified and/or licensed to practice in a particular medical field, medical specialty, and/or in a particular set of geographical jurisdictions. By creating the physician profile, a set of rules are created that only allow that physician to be assigned to slots and medical tasks for which the physician is qualified. If a user of the workflow tool attempts to assign a physician to a slot or task for which the physician is not qualified, a violation can be triggered and the user can be notified that the physician is unavailable to be assigned to that slot or task.

Similarly, slot assignment rules can be based on geographical location and time considerations. A physician may be only available to be assigned to slots within a certain geographical area, e.g., within a certain distance from a city or other geographical center. A physician can also specify that he or she is unavailable during a certain time period (e.g., a vacation time), or limits can be placed on the number of hours that a physician can work during a specific time span. If a user of the workflow tool attempts to assign a physician to a slot that is outside the physician's defined geographical area, a violation can be triggered that notifies that user that the physician is unavailable for that slot due to geographical constraints. Similarly, if a user attempts to assign a physician to a slot that occurs during a time when the physician is unavailable or that exceeds the number of hours that a physician can work during a defined time period (e.g., one week), a similar violation can be triggered. In certain circumstances, users with the appropriate permissions can override slot assignment rules to accommodate particular extenuating circumstances, such as a physician assigned to a particular slot being unavailable due to poor health. This enables schedulers to ensure that slots and medical tasks are distributed evenly and that particular medical resources are neither over-utilized nor under-utilized, while maintaining the ability to override slot assignment rules in appropriate circumstances.

In the context of workflow tool 112, the enforcement of slot assignment rules can include feedback that flows between resource scheduler 215 and workflow dispatcher 216. If a user of workflow dispatcher 216 attempts to assign a task or medical resource to a slot, the attempted assignment can be forwarded to resource scheduler 215 for verification. If the attempted assignment violates a medical resource parameter and/or a slot parameter, an assignment rule violation can be triggered and notice of the violation returned to the workflow dispatcher. In some instances, the user of the workflow dispatcher can determine an alternate medical resource and/or slot for the assignment. As mentioned above, a user with the appropriate permissions may be able to override a slot assignment rule and assign the medical resource to the slot despite the assignment rule violation.

Figure 31:
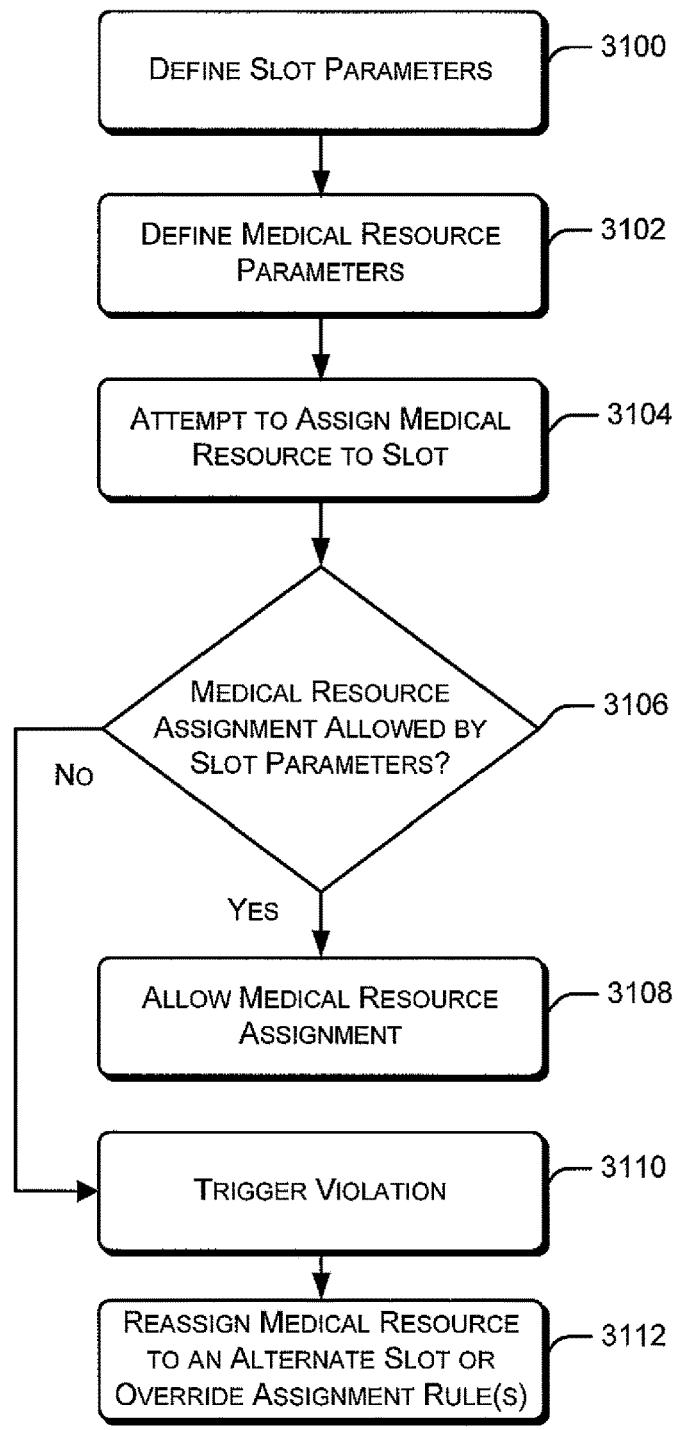
FIG. 31 is a flow diagram of a process for assigning a medical resource to a slot in accordance with one or more embodiments.

FIG. 31 illustrates one example of a process that can utilize resource scheduler 215 in accordance with one or more embodiments. At 3100, parameters for a particular slot are defined. At 3102, parameters for a particular medical resource are defined. At 3104, an attempt is made to assign the medical resource to the slot. At 3106, it is determined if the slot parameters and/or medical resource parameters allow the medical resource to be assigned to the slot. If the medical resource is available to be assigned to the slot, then the medical resource is assigned to the slot at 3108. If the medical resource is not available to be assigned to the slot, then an assignment violation is triggered at 3110. Act 3110 can include the display of an interface and/or popup window to a user that indicates that an assignment violation has occurred. At 3112, an alternate medical resource (whose parameters match the slot) is assigned to the slot, or alternatively, one or more slot and/or medical resource parameters are overridden and the original medical resource is assigned to the slot.

Conclusion

The described processes and techniques provide participants in a medical workflow with an integrated way to interact with a variety of medical information systems. Medical information can be collected from different medical information systems and/or data sources and presented to a user in one or more customized interfaces. Users can interact with the interface(s) and perform tasks associated with a medical workflow.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A system comprising:
one or more hardware processors; and
one or more non-transitory computer-readable storage media storing computer-executable instructions that are executable by the one or more hardware processors;
a structured data acquisition tool executable by the one or more processors to perform operations including wrapping an external graphical user interface (GUI) of a first medical information application that is external to the structured data acquisition tool such that user interaction with the external GUI is detectable by the structured data acquisition tool, the first medical information application managed by a first medical information system containing, for each of a plurality of medical records, medical workflow data, wherein a particular medical record of the plurality of medical records is configured to be displayed within the external GUI;
a second medical information application managed by a second medical information system that is external to the first medical information system, the second medical information application executable by the one or more processors to perform operations including:
receiving from the structured data acquisition tool a notification indicating a user selection of the particular medical record from the external GUI of the first medical information application;
responsive to receiving the notification from the structured data acquisition tool, performing operations including:
launching a form in a local GUI of the second medical information application the local GUI being separate from the external GUI of the first medical information application;
utilizing the form to automatically capture the medical workflow data from the particular medical record of the first medical information application, including capturing text from particular the medical record included in the external GUI;
automatically populating the form within the local GUI with the medical workflow data such that at least some of the medical workflow data is displayed in the form, including automatically populating the text captured from the external GUI to the local GUI;
receiving user input to the form within the local GUI of the second medical information application, the user input including an edit of the text populated to the local GUI from the external GUI; and
causing the particular medical record managed by the first medical information application to be automatically updated based on the input by the user into the form by pushing the edited text from the local GUI of the second medical information application to the first medical information application of the first medical information system such that the updated medical record with the edited text is accessible via the external GUI of the first medical information application.

2. A system as recited in claim 1, wherein the system further comprises an aggregator module executable by the one or more processors to perform operations including receiving the medical workflow data from the first medical information application, and wherein the aggregator module includes a message broker that determines whether the medical workflow data is to be forwarded to one or more external entities.

3. A system as recited in claim 2, wherein the aggregator module includes a data flow controller that is executable by the one or more processors to perform operations including performing normalization of medical workflow data.

4. A system as recited in claim 1, wherein the system further comprises a dictionary processor module executable by the one or more processors to perform operations including receiving a plurality of medical codes from external medical information systems and correlating each of the plurality of medical codes with a common medical procedure.

5. A system as recited in claim 1, wherein the second application implements the structured data acquisition tool.

6. A system as recited in claim 1, wherein the structured data acquisition tool is executable by the one or more processors to perform operations including utilizing the form to capture other medical workflow data from at least one other medical information application, and wherein the system further include a workflow tool module executable by the one or more processors to perform operations including automatically populating the form with at least some of the other medical workflow data.

7. A system as recited in claim 1, wherein the structured data acquisition tool is further executable by the one or more processors to perform operations including utilizing the form to capture other medical workflow data from an external medical information system, and automatically populating the form with at least some of the other medical workflow data.

8. A system as recited in claim 1, wherein the second medical information application is further configured to perform operations including generating the form in response to detecting a user selection of an external instance of the medical record.

9. A system as recited in claim 8, wherein the external instance of the medical record is maintained by an external medical information application.

10. A system as recited in claim 9, wherein the structured data acquisition tool is further executable by the one or more processors to perform operations including updating the external instance of the medical record in response to a user saving changes made to the form.

11. A system as recited in claim 1, wherein the system further comprises a workflow tool module executable by the one or more processors to perform operations including monitoring a pending medical procedure and automatically triggering an alert if the pending medical procedure exceeds an allowed pending time.

12. A system as recited in claim 11, wherein the workflow tool module is further executable by the one or more processors to perform operations including enforcing assignment rules that specify whether a particular medical task is assignable to a particular medical resource.

13. A system as recited in claim 1, wherein the system further comprises a resource scheduler module executable by the one or more processors to perform operations including causing a medical resource to be automatically scheduled to perform a medical procedure in response to the user interaction with the first medical information application.

14. A system as recited in claim 1, wherein the system further comprises a workflow analytics module executable by the one or more processors to perform operations including performing a statistical analysis utilizing the medical workflow data and reassigning a medical procedure based on the statistical analysis indicating that one or more of medical personnel or a medical facility is behind schedule.

15. A system as recited in claim 1, wherein the system further comprises a workflow tool module executable by the one or more processors to perform operations including pushing the updated medical record to an entity as at least one of a new medical task or a new medical workflow.

16. A system as recited in claim 1, wherein the system further comprises a workflow tool module executable by the one or more processors to perform operations including pushing the updated medical record to an entity as at least one of an update to an existing medical task or an update to an existing medical workflow.

17. A system as recited in claim 1, wherein the user input to the form causes a change to the medical workflow data, and wherein the system further comprises a message broker module executable by the one or more processors to perform operations including ascertaining whether the change to the medical workflow data is to be forwarded to the first medical information application.

18. A system as recited in claim 1, wherein the computer-executable instructions are executable by the one or more hardware processors to perform operations comprising:
receiving an indication that the user performs a login to the first medical information application; and
causing, automatically and responsive to the login to the first medical information application, the user to be logged into the structured data acquisition tool.

19. A computer-implemented method comprising:
wrapping, by a local medical information application of a local medical information system, an external graphical user interface (GUI) of an external medical information application that is external to a computing system that implements the local medical information system such that user interaction with the external GUI is detectable by the local medical information application;
receiving, by the computing system, a signal indicating a user selection of a medical record from the external GUI that is external to the computing system;
launching, by the computing system, a form in a local GUI of the local medical information application that is separate from the external GUI, said launching occurring automatically by the local medical information application and in response to detecting the user selection of the medical record from the external GUI;
utilizing, by the computing system, the form to capture medical workflow data from the medical record of the external medical information application that is external to the computing system, the medical workflow data including text content from the external GUI;
automatically populating, by the computing system, the form in the local GUI with the medical workflow data in response to a user interaction with the external medical information application such that at least some of the medical workflow data is displayed in the form;
receiving, by the computing system, user input to the local GUI to edit the text content; and
updating, by the computing system, the medical record based on input by the user into the form in the local GUI by pushing the edited text content from the local medical information application to the external medical information application.

20. A computer-implemented method comprising:

utilizing, by a computing system, a form in a local graphical user interface (GUI) to capture medical workflow data from an external medical information application by wrapping an external graphical user interface (GUI) of the external medical information application that is external to the computing system such that user interaction with the external GUI is detectable by the computing system;

automatically populating, by the computing system, the form in the local GUI with the medical workflow data in response to an interaction by a user with the external medical information application such that at least some of the medical workflow data is displayed as part of the form in the local GUI;

automatically updating, by the computing system, one or more external instances of a medical record based on input by the user into the form by pushing the input to the one or more external instances of the medical record;

performing a statistical analysis utilizing the medical workflow data to determine that a medical procedure assigned to a particular entity and associated with the one or more external instances of the medical record is behind schedule;

generating an alert indicating that the medical procedure is behind schedule based on one or more of the procedure approaching an allowed pendency time, or the procedure exceeding the allowed pendency time; and reassigning, automatically and in response to the alert, the medical procedure to a different entity that is indicated as being available to perform the procedure.

* * * * *